US011236142B2

(12) United States Patent
Yang et al.

(10) Patent No.: US 11,236,142 B2
(45) Date of Patent: Feb. 1, 2022

(54) ACYLATED OXYNTOMODULIN PEPTIDE ANALOG

(71) Applicant: DONG-A ST CO., LTD., Seoul (KR)

(72) Inventors: Jae-Sung Yang, Seoul (KR); Kyung-Seok Lee, Yongin-si (KR); Yu-Na Chae, Yongin-si (KR); Gye-Rim Baek, Yongin-si (KR); Tae-Hyoung Kim, Seoul (KR); Ill-Hun Jung, Anyang-si (KR); Chae-Lim Ryu, Seongnam-si (KR); Weon-Bin Im, Yongin-si (KR)

(73) Assignee: DONG-A ST CO., LTD., Seoul (KR)

( * ) Notice: Subject to any disclaimer, the term of this patent is extended or adjusted under 35 U.S.C. 154(b) by 0 days.

(21) Appl. No.: 16/638,970

(22) PCT Filed: Aug. 16, 2018

(86) PCT No.: PCT/KR2018/009425
§ 371 (c)(1),
(2) Date: Feb. 13, 2020

(87) PCT Pub. No.: WO2019/035672
PCT Pub. Date: Feb. 21, 2019

(65) Prior Publication Data
US 2020/0354425 A1    Nov. 12, 2020

(30) Foreign Application Priority Data

Aug. 16, 2017    (KR) .................. 10-2017-0103798
Aug. 16, 2018    (KR) .................. 10-2018-0095717

(51) Int. Cl.
| | | |
|---|---|---|
| A61K 38/00 | (2006.01) | |
| C07K 14/575 | (2006.01) | |
| A61P 3/04 | (2006.01) | |
| A61P 3/10 | (2006.01) | |

(52) U.S. Cl.
CPC .............. *C07K 14/575* (2013.01); *A61P 3/04* (2018.01); *A61P 3/10* (2018.01); *A61K 38/00* (2013.01)

(58) Field of Classification Search
None
See application file for complete search history.

(56) References Cited

FOREIGN PATENT DOCUMENTS

| KR | 10-2012-0139579 A | 12/2012 |
|---|---|---|
| WO | 2016/049190 A1 | 3/2016 |
| WO | WO 2016/049190 | * 3/2016 |

OTHER PUBLICATIONS

Kazuhisa Honda, "Glucagon-related peptides and the regulation of food intake in chickens", Animal Science Journal, 2016, vol. 87, pp. 1090-1098.
Jens Juul Holst, "The Physiology of Glucagon-like Peptide 1", Physiol. Rev., Oct. 2007, vol. 87, pp. 1409-1439.
Eva Winning Iepsen et al., "Liraglutide for Type 2 diabetes and obesity: a 2015 update", Expert Rev. Cardiovasc. Ther., 2015, vol. 13, No. 7, pp. 753-767.
Young Sil Eom et al., "Glucagon-Like Peptide-1 (GLP-1) Agonist", The Korean Journal of Medicine, 2014, vol. 87, No. 1, pp. 9-13.
Alessandro Pocai et al., "Glucagon-Like Peptide 1/Glucagon Receptor Dual Agonism Reverses Obesity in Mice", Diabetes, Oct. 2009, vol. 58, pp. 2258-2266.
Katie Wynne et al., "Subcutaneous Oxyntomodulin Reduces Body Weight in Overweight and Obese Subjects", Diabetes, Aug. 2005, vol. 54, pp. 2390-2395.
Diabetes, 2013;62(Suppl. 1):A48 (99 pages).
Mark A. Cohen et al., "Oxyntomodulin Suppresses Appetite and Reduces Food Intake in Humans", The Journal of Clinical Endocrinology & Metabolism, 2003, vol. 88, No. 10, pp. 4696-4701.
Alessandro Pocai, "Action and therapeutic potential of oxyntomodulin", Molecular Metabolism, 2014, vol. 3, pp. 241-251.
Lan Zhu et al., "The Role of Dipeptidyl Peptidase IV in the Cleavage of Glucagon Family Peptides", The Journal of Biological Chemistry, Jun. 20, 2003, vol. 278, No. 25, pp. 22418-22423.
Brian P. Ward et al., "Peptide lipidation stabilizes structure to enhance biological function", Molecular Metabolism, 2013, vol. 2, pp. 468-479.
Avinash Muppidi et al., "Design of Potent and Proteolytically Stable Oxyntomodulin Analogs", ACS Chemical Biology, 2016, vol. 11, pp. 324-328.
S. J. Henderson PhD et al., "Robust anti-obesity and metabolic effects of a dual GLP-1/glucagon receptor peptide agonist in rodents and non-human primates", Diabetes, Obesity and Metabolism, Dec. 2016, vol. 18, pp. 1176-1190.
Philip Ambery et al., "MEDI0382, a GLP-1 and glucagon receptor dual agonist, in obese or overweight patients with type 2 diabetes: a randomised, controlled, double-blind, ascending dose and phase 2a study", Lancet, Jun. 30, 2018, vol. 391, pp. 2607-2618.
Joakim E. Swedberg et al., "Cyclic alpha-conotoxin peptidomimetic chimeras as potent GLP-1R agonist", European Journal of Medicinal Chemistry, 2015, vol. 103, pp. 175-184.
Eunice N. Murage et al., "Search for α-helical propensity in the receptor-bound conformation of glucagon-like peptide-1", Bioorganic & Medicinal Chemistry, 2008, vol. 16, pp. 10106-10112.
Les P. Miranda et al., "Design and Synthesis of Conformationally Constrained Glucagon-Like Peptide-1 Derivatives with Increased Plasma Stability and Prolonged in Vivo Activity", J. Med. Chem., 2008, vol. 51, No. 9, pp. 2758-2765.
International Search Report dated Nov. 23, 2018, issued by the International Searching Authority in application No. PCT/KR2018/009425.

* cited by examiner

*Primary Examiner* — Sergio Coffa
(74) *Attorney, Agent, or Firm* — Sughrue Mion, PLLC

(57) ABSTRACT

The present invention relates to a novel peptide analog of acylated oxyntomodulin and a pharmaceutical composition comprising the same for preventing and treating obesity or overweightness, or diabetes accompanied by obesity and overweightness. The peptides are superior to those of natural oxyntomodulin in dual agonism on GLP-1 and glucagon receptors and longer in vivo half-life. A pharmaceutical composition comprising said peptides is effective in the treatment of metabolic diseases such as obesity and diabetes mellitus.

9 Claims, 15 Drawing Sheets
Specification includes a Sequence Listing.

[Figure 1]
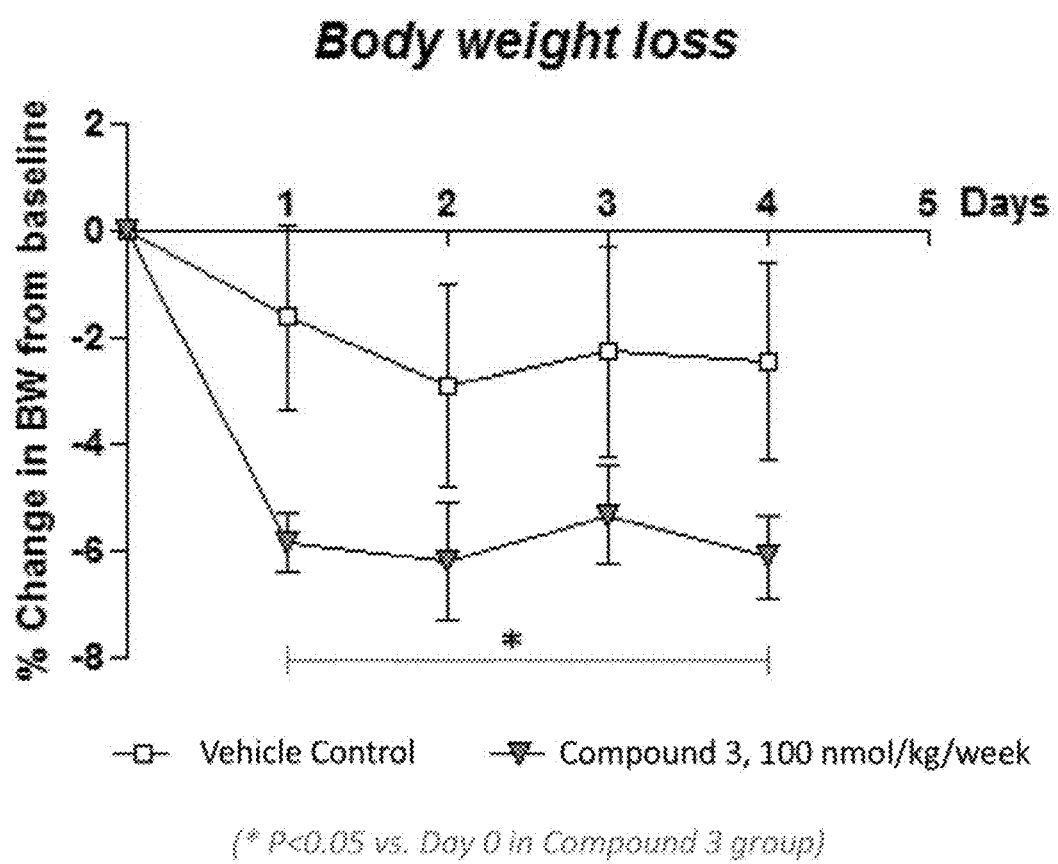

[Figure 2a]
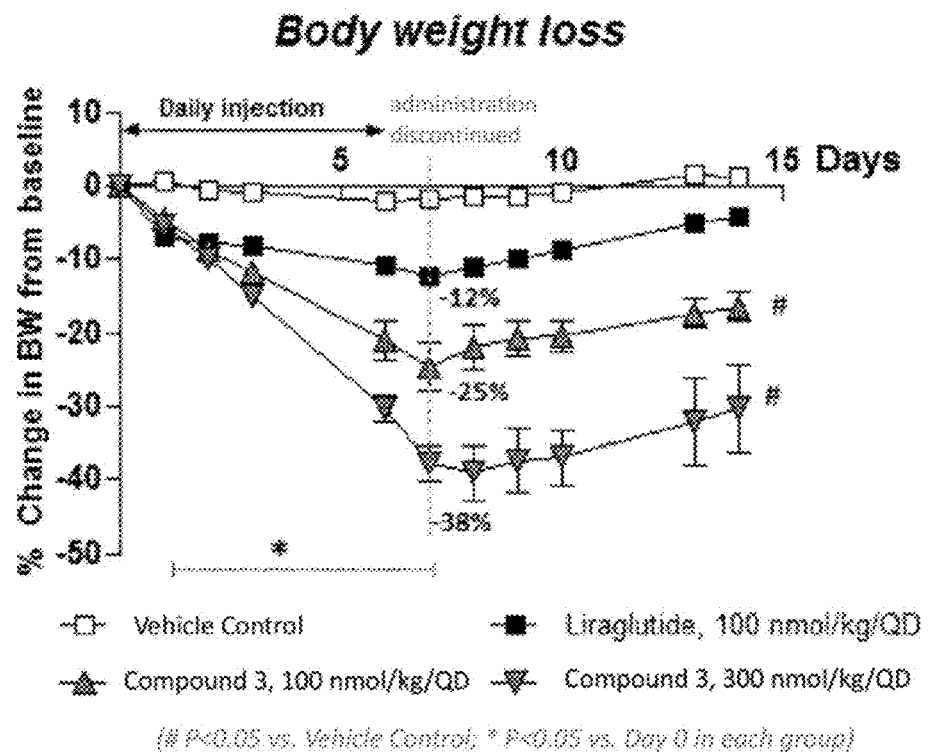
[Figure 2b]
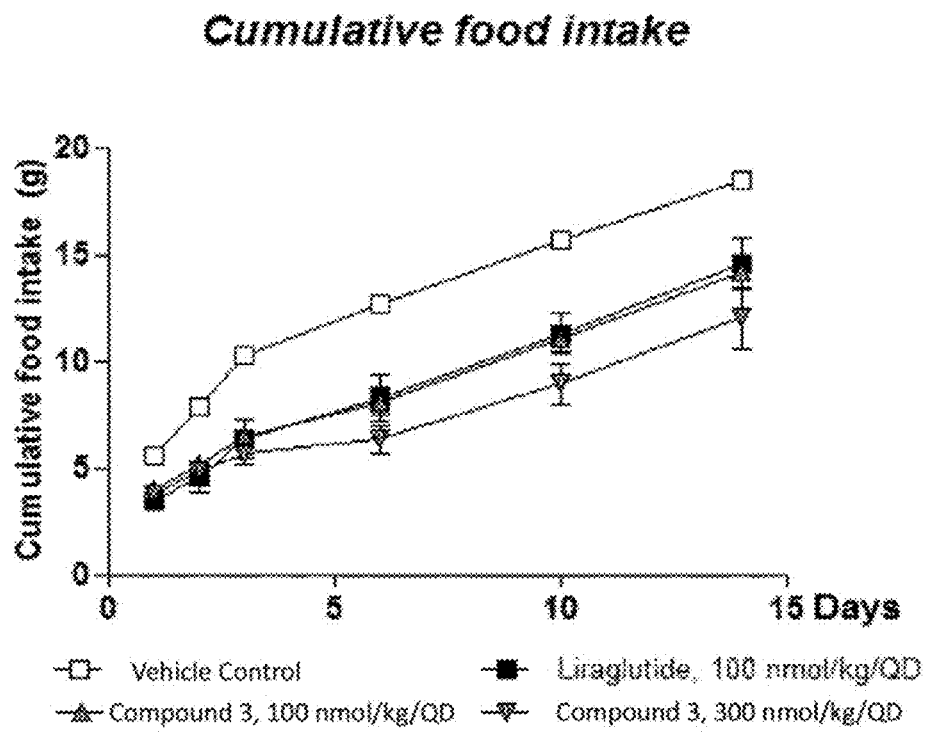

[Figure 3a]
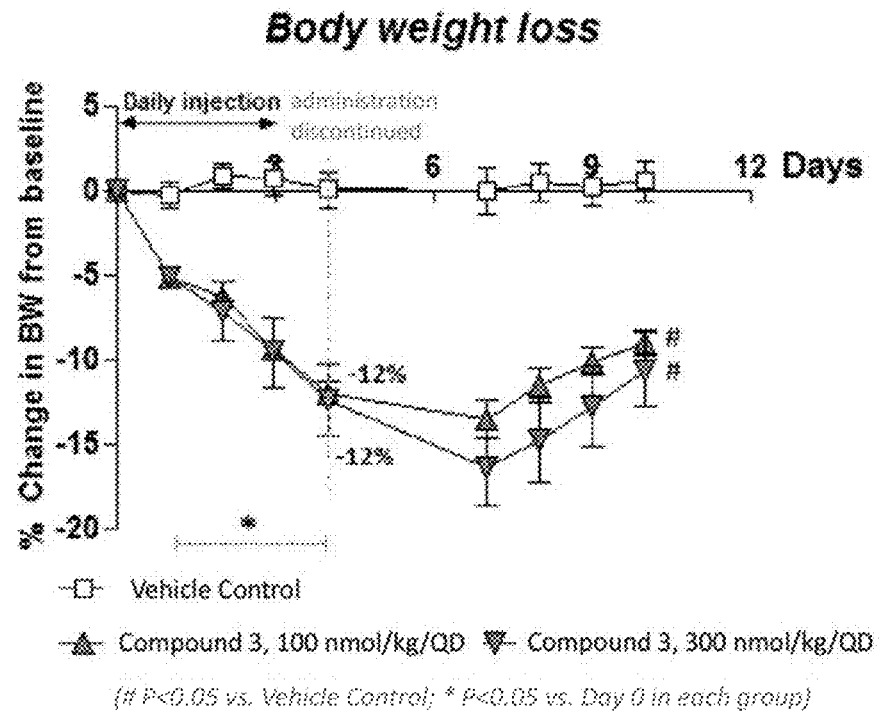
[Figure 3b]
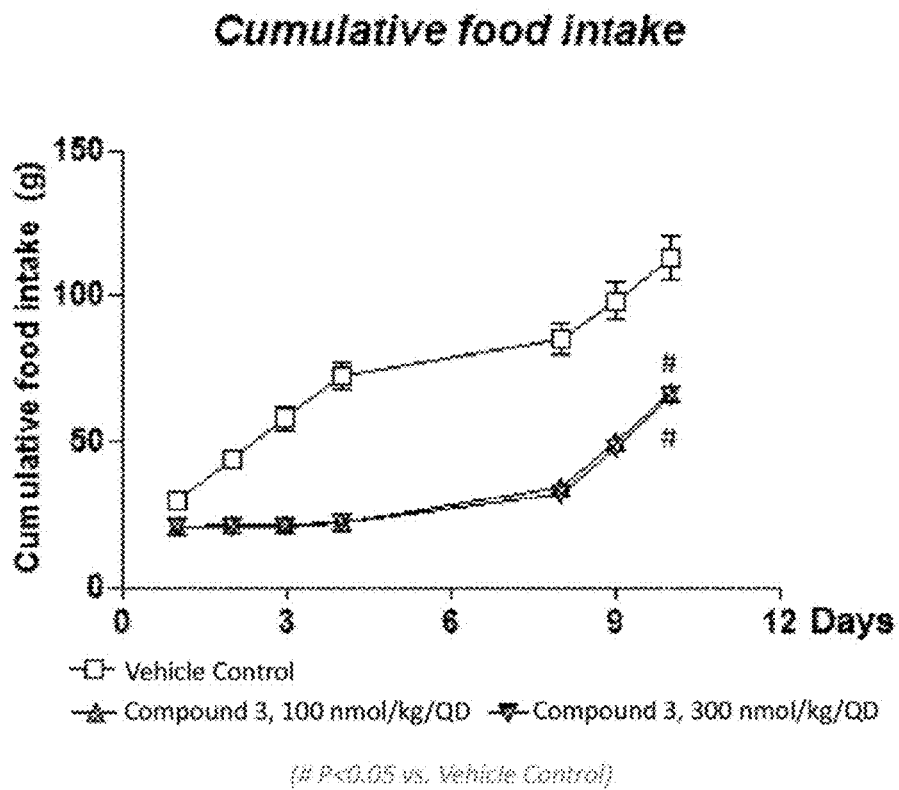

[Figure 4a]
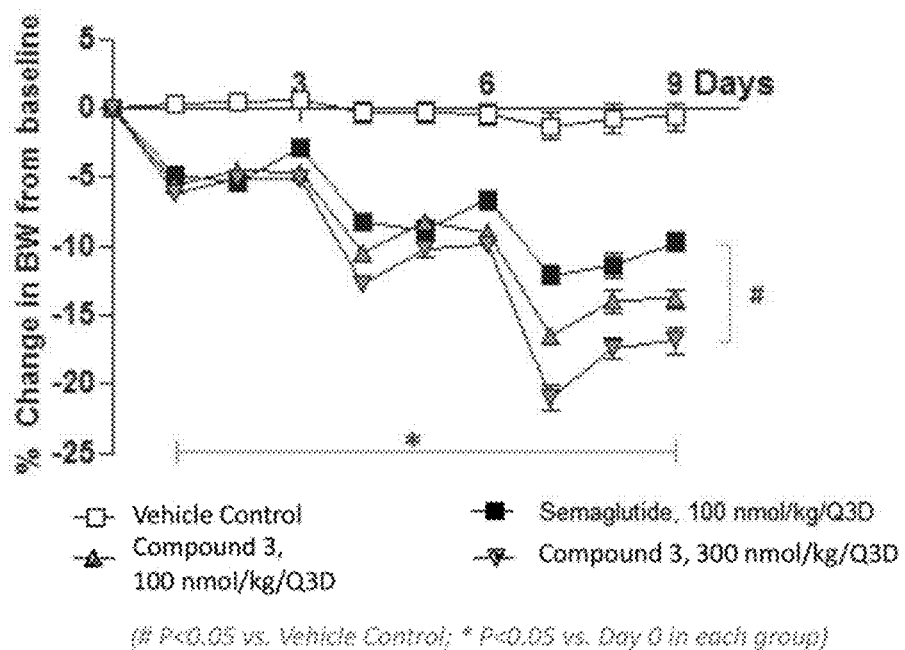
[Figure 4b]
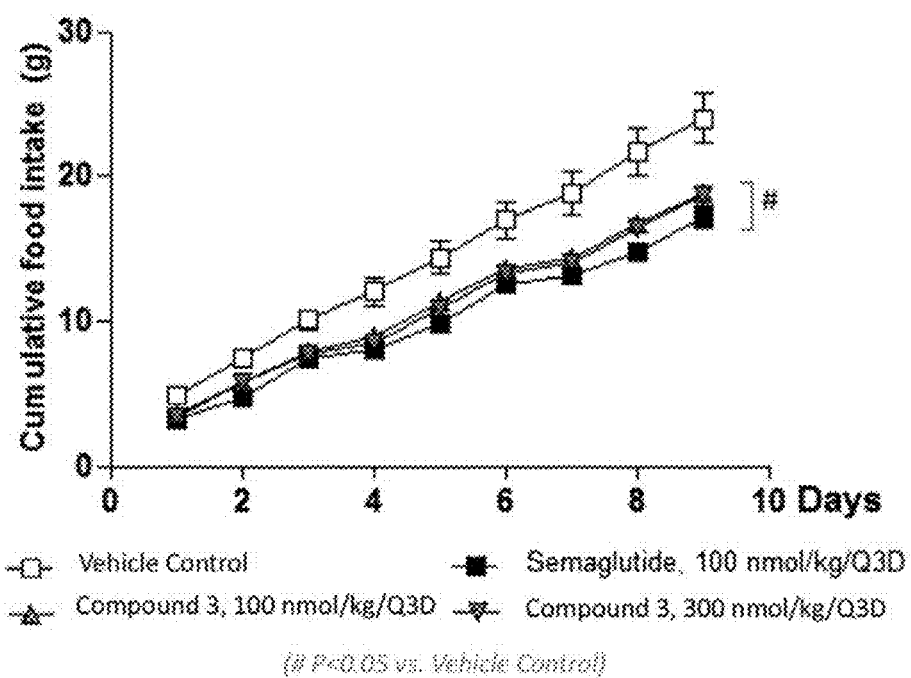

[Figure 5a]
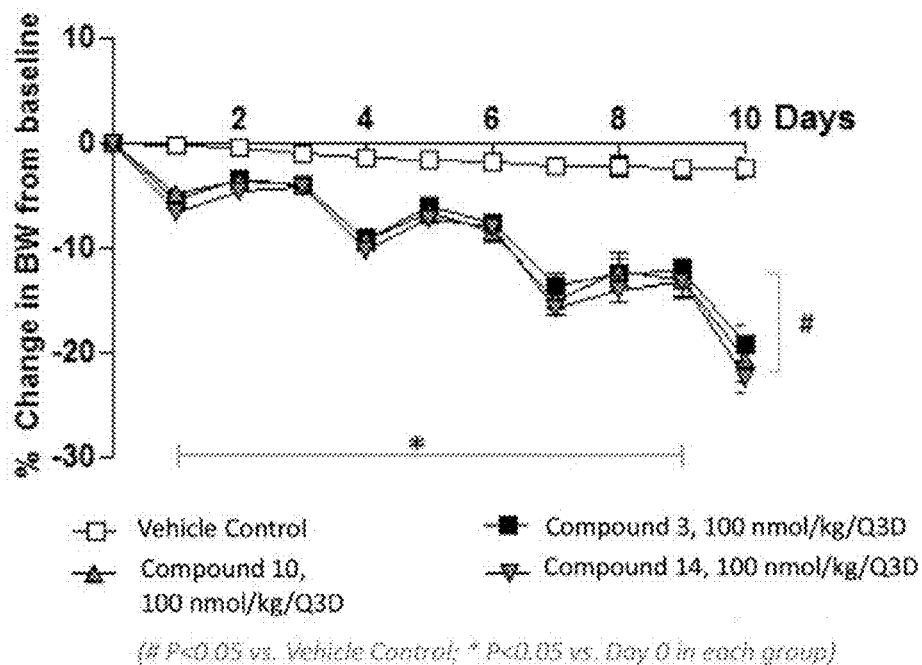
[Figure 5b]
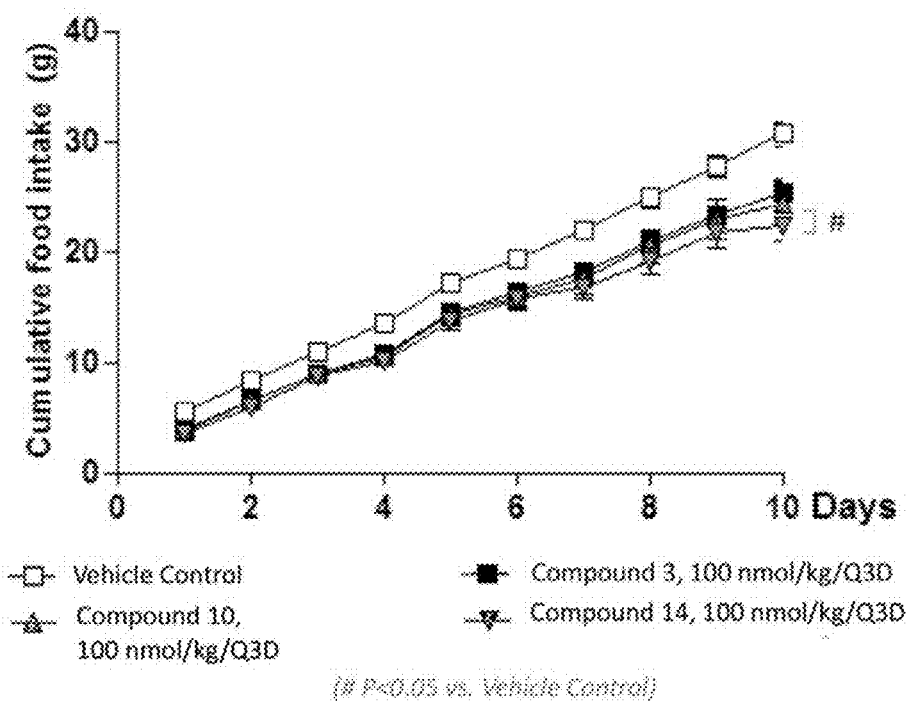

[Figure 6a]
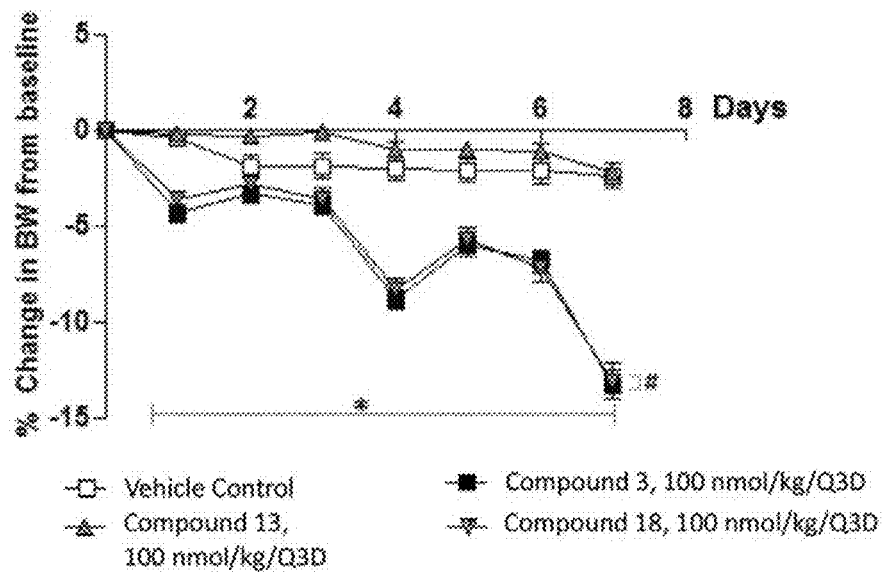
(# P<0.05 vs. Vehicle Control; * P<0.05 vs. Day 0 in Compounds 3 & 18)
[Figure 6b]
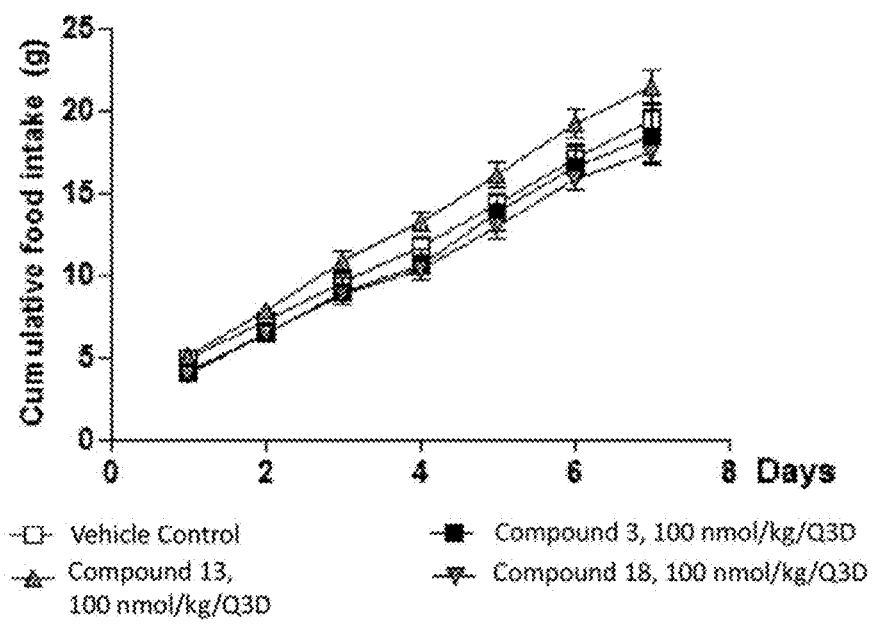

[Figure 7a]
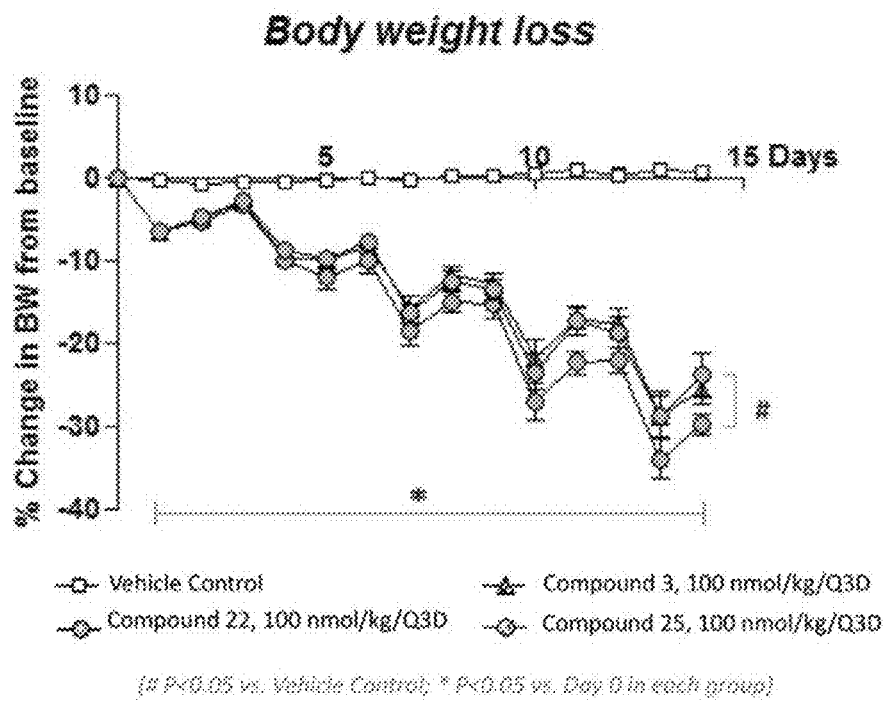
[Figure 7b]
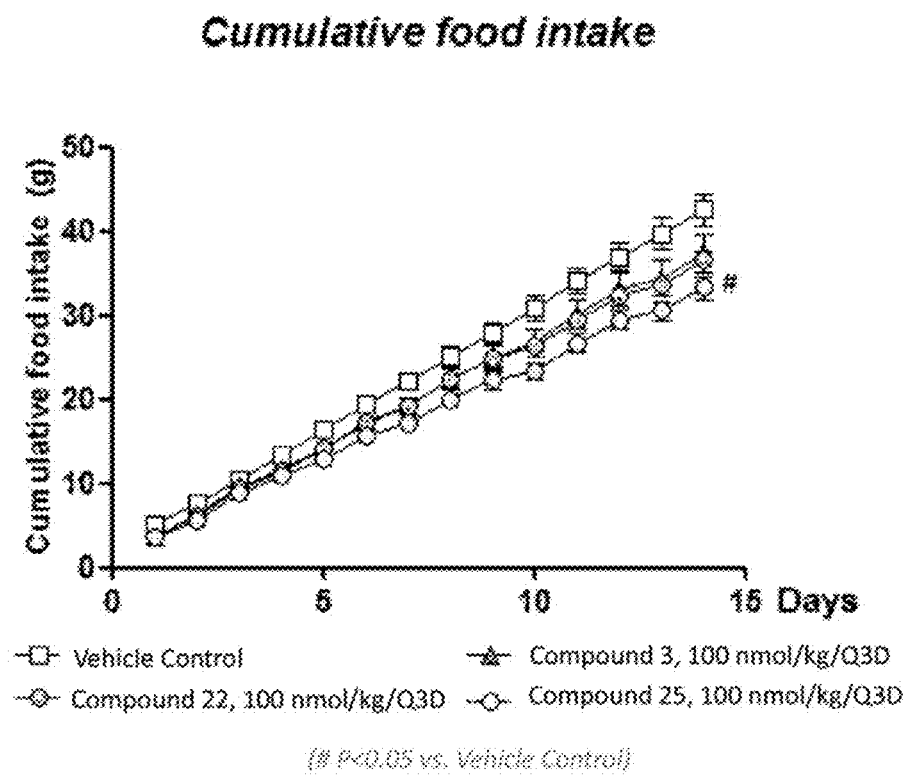

[Figure 7c]
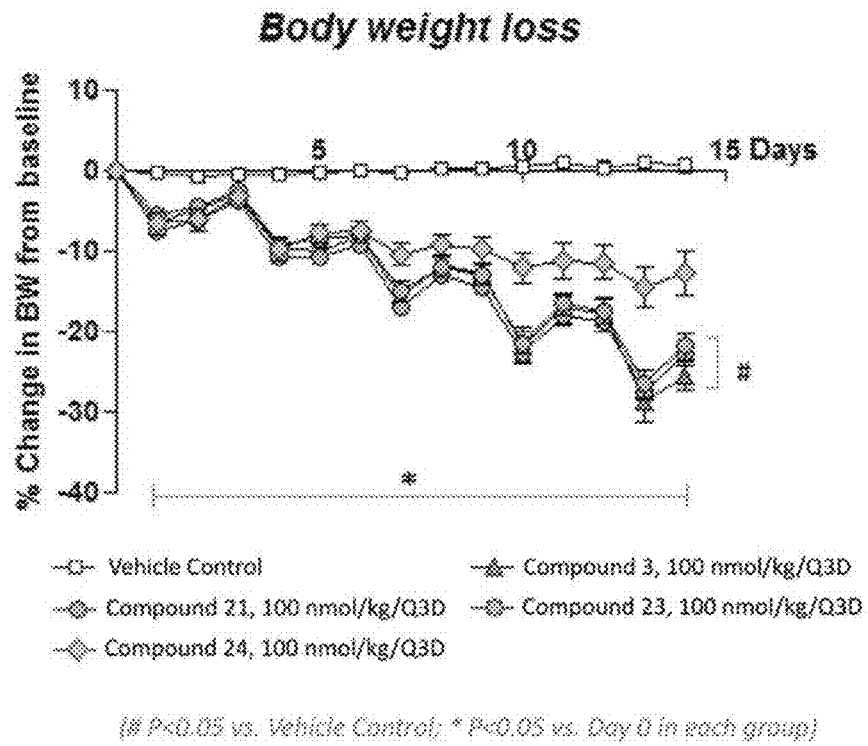
(# P<0.05 vs. Vehicle Control; * P<0.05 vs. Day 0 in each group)
[Figure 7d]
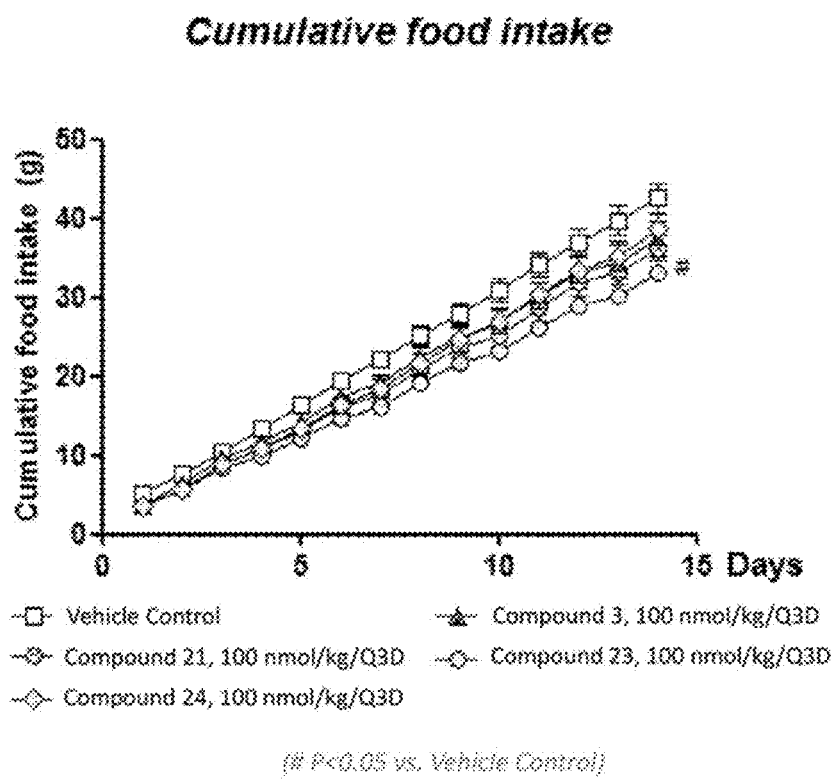
(# P<0.05 vs. Vehicle Control)

[Figure 8a]
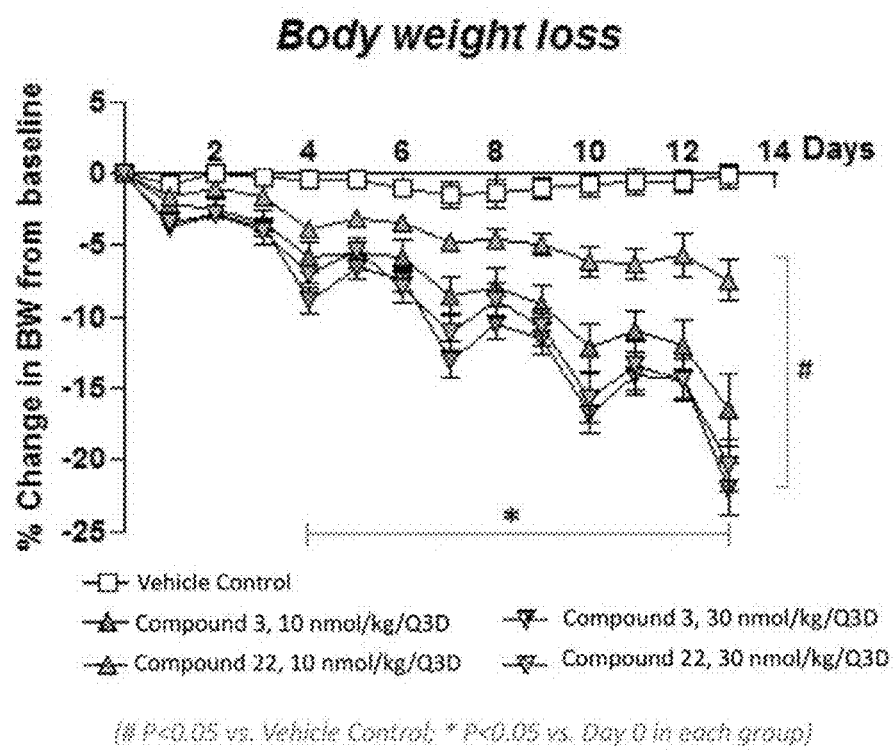

[Figure 8b]
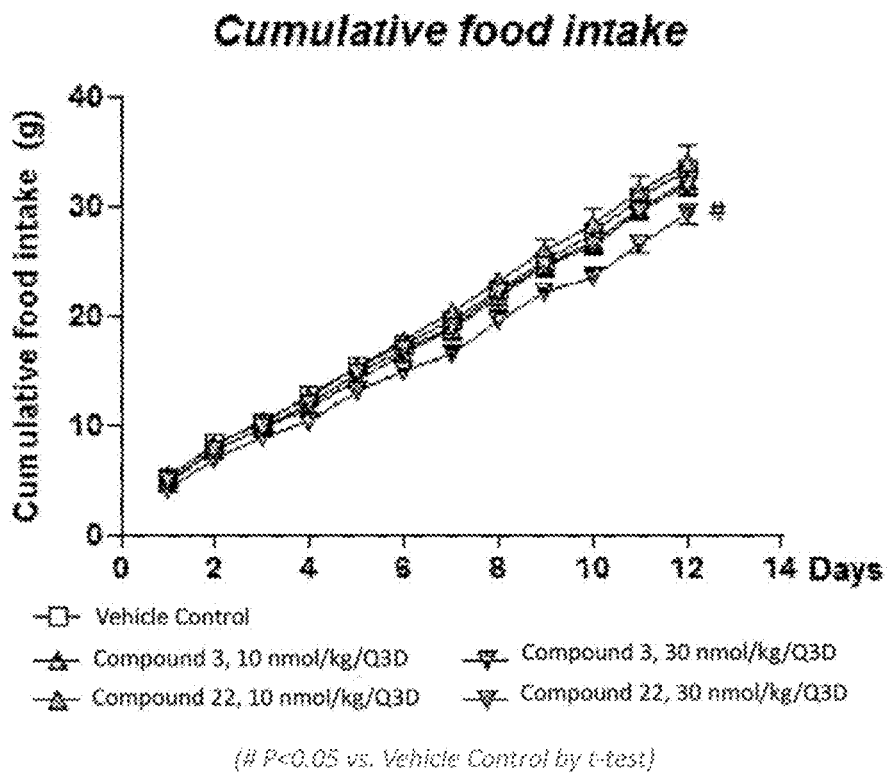
(# P<0.05 vs. Vehicle Control by t-test)
[Figure 9a]
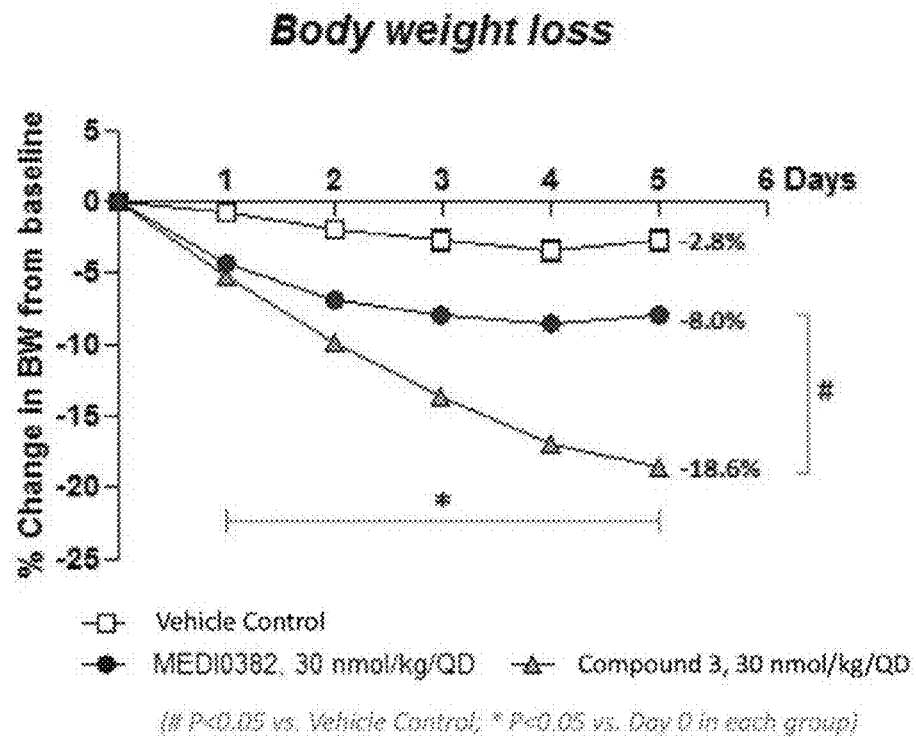
(# P<0.05 vs. Vehicle Control; * P<0.05 vs. Day 0 in each group)

[Figure 9b]
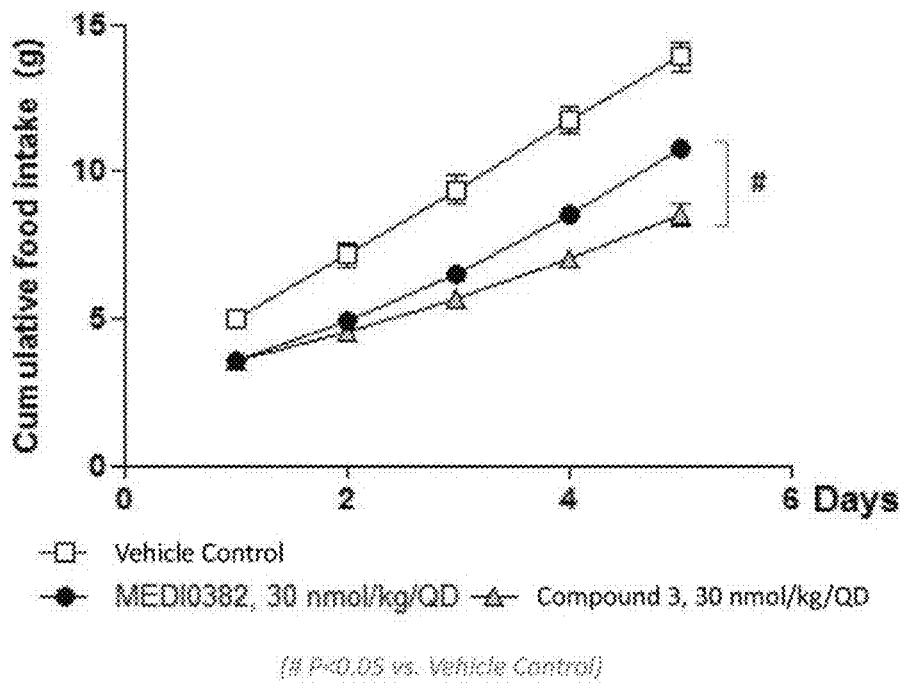
[Figure 10a]
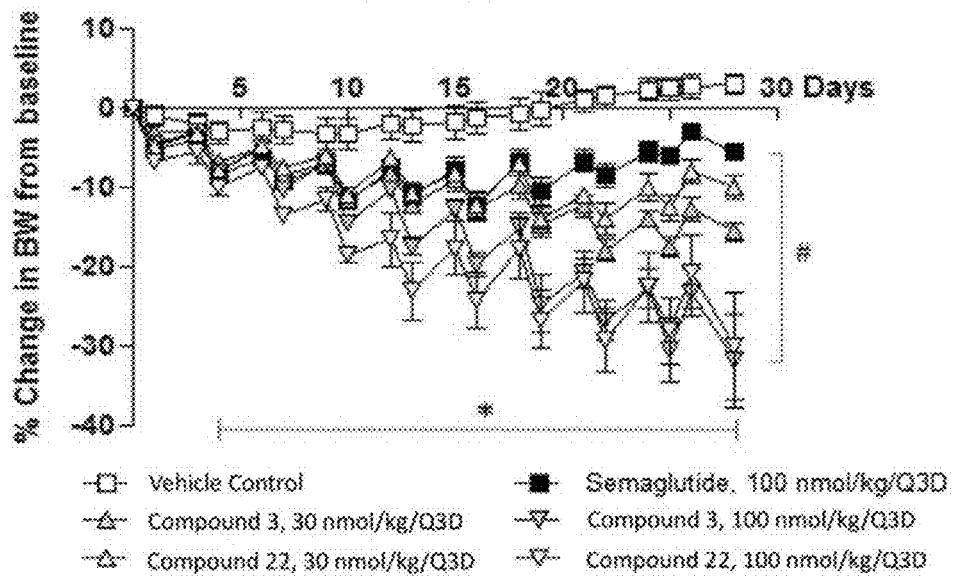

[Figure 10b]
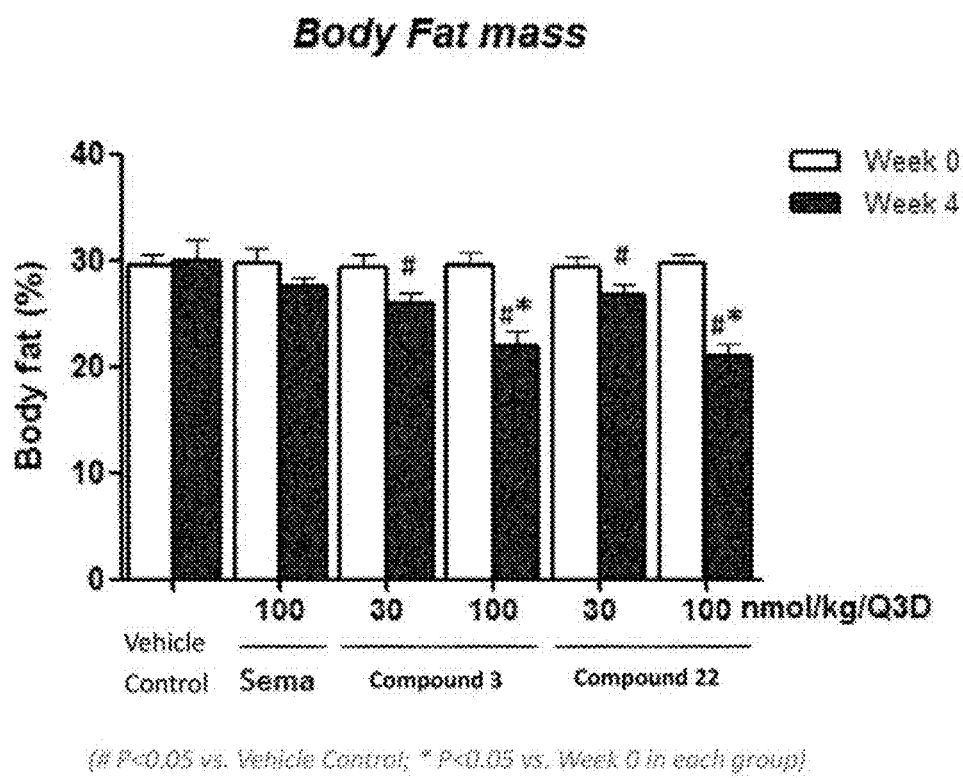

[Figure 10c]
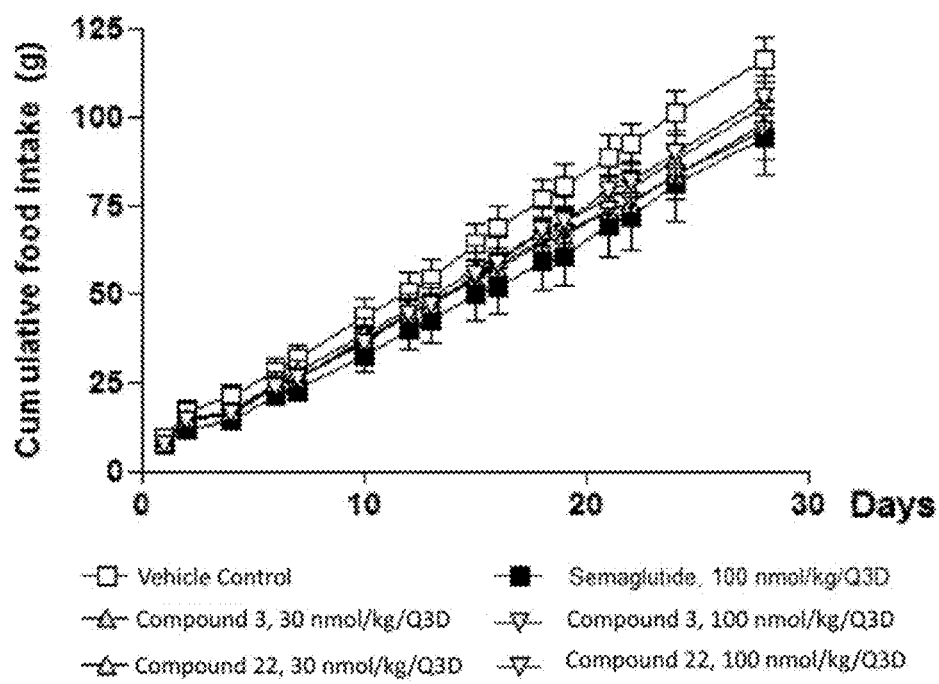
[Figure 11]
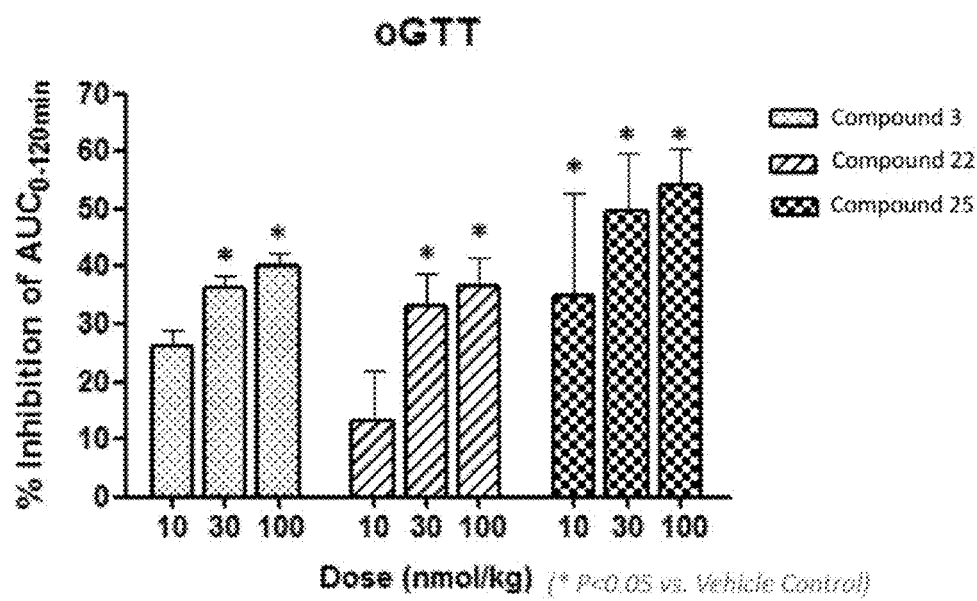

[Figure 12a]
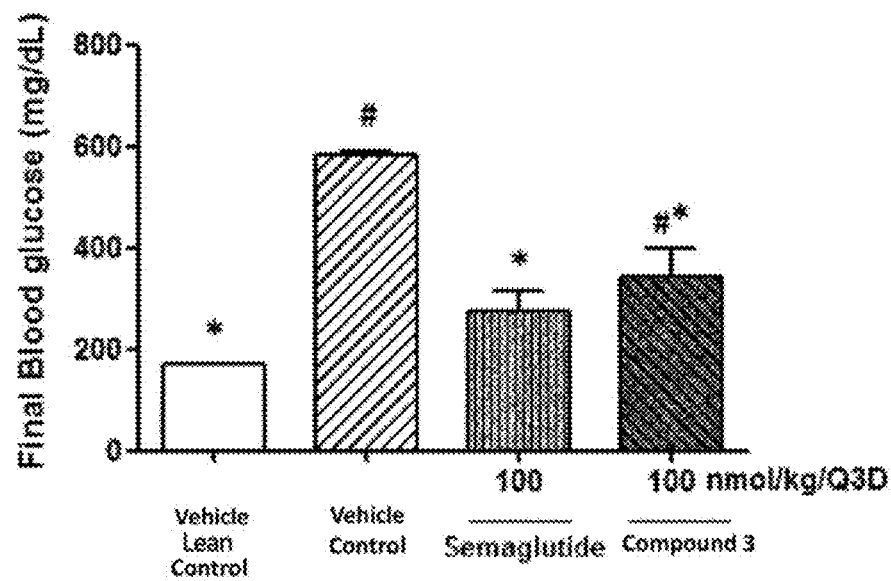
[Figure 12b]
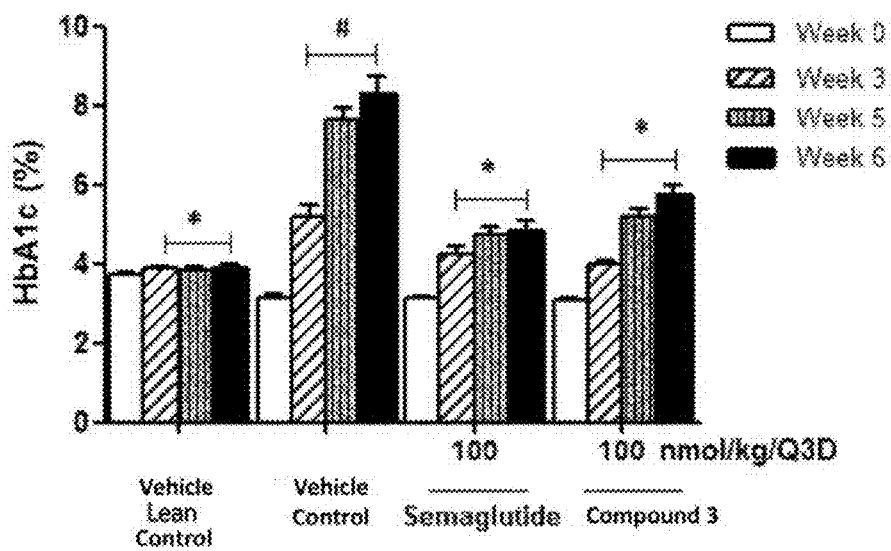

[Figure 13a]
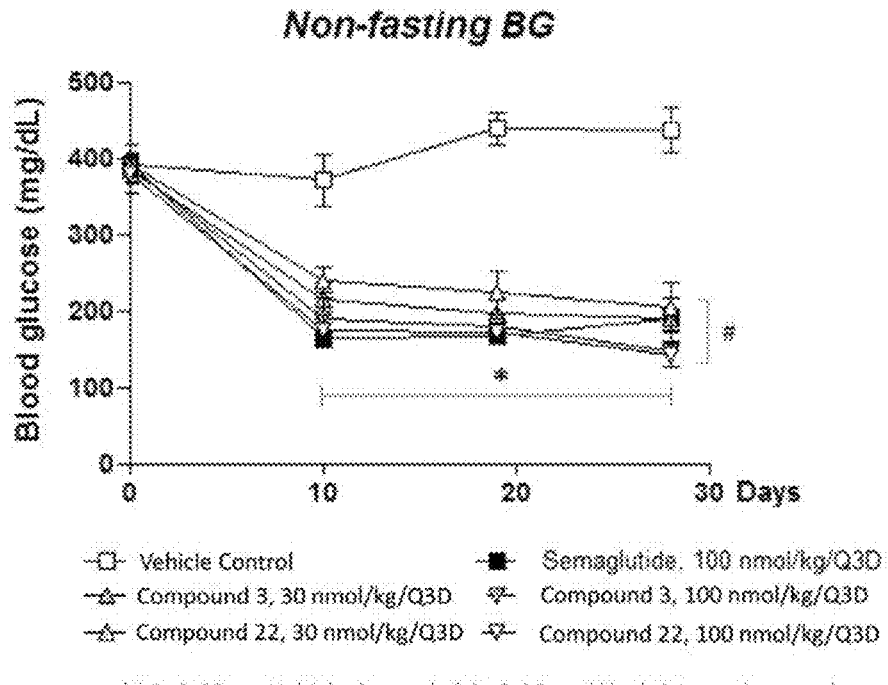
[Figure 13b]
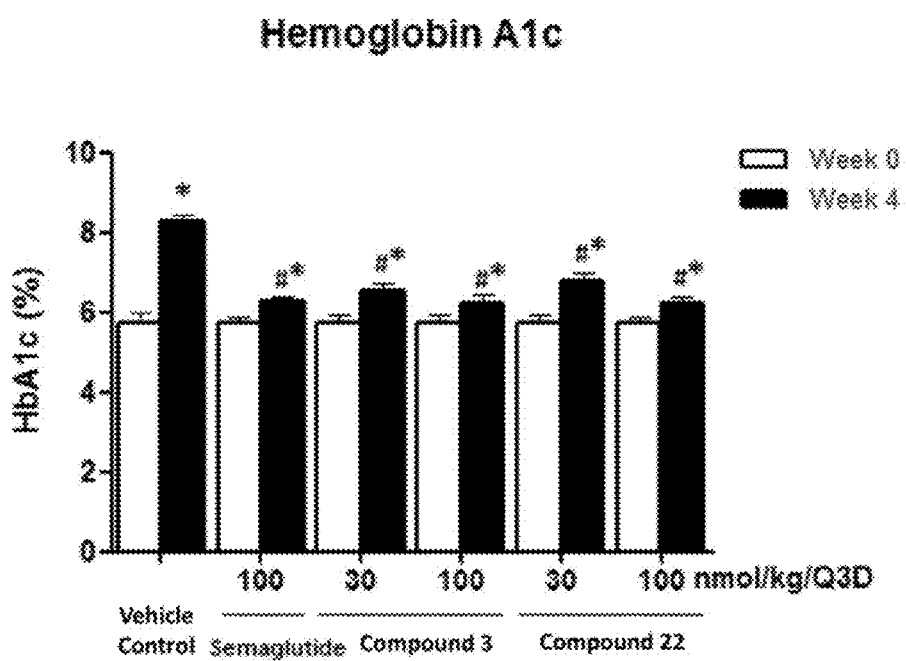

SEQUENCE LISTING

<160> NUMBER OF SEQ ID NOS: 53

<210> SEQ ID NO 1
<211> LENGTH: 37
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 30
<212> TYPE: PRT
<213> ORGANISM: Artificial Sequence
<220> FEATURE:
<223> OTHER INFORMATION: oxyntomodulin analogue
<220> FEATURE:

```
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])

<400> SEQUENCE: 2

His Ser Gln Gly Thr Phe Thr Ser Asp Xaa Ser Lys Tyr Leu Asp Ser
1               5                   10                  15

Arg Arg Ala Gln Asp Phe Val Gln Trp Leu Met Asn Thr Lys
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])

<400> SEQUENCE: 3

His Xaa Gln Gly Thr Phe Thr Ser Asp Xaa Ser Lys Tyr Leu Asp Ser
1               5                   10                  15

Arg Arg Ala Gln Asp Phe Val Gln Trp Leu Met Asn Thr Lys
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 4

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
```

```
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (30)
<223> OTHER INFORMATION: AMIDATION, C-terminal amidation

<400> SEQUENCE: 5

His Ser Gln Gly Thr Phe Thr Ser Asp Xaa Ser Lys Tyr Leu Asp Ser
1               5                   10                  15

Arg Arg Ala Gln Asp Phe Val Gln Trp Leu Met Asn Thr Lys
            20                  25                  30

<210> SEQ ID NO 6
<211> LENGTH: 37
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])

<400> SEQUENCE: 6

His Ser Gln Gly Thr Phe Thr Ser Asp Xaa Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 7
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)
<223> OTHER INFORMATION: Xaa=aminoisobutyric acid
<220> FEATURE:
<221> NAME/KEY: MOD_RES
<222> LOCATION: (30)
<223> OTHER INFORMATION: AMIDATION, C-terminal amidation

<400> SEQUENCE: 7

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 8
<211> LENGTH: 37
```

```
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 8

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 9
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[icosanoyl])
<220> FEATURE:
<221> NAME/KEY: MOD_RES
<222> LOCATION: (16)
<223> OTHER INFORMATION: Xaa=aminoisobutyric acid

<400> SEQUENCE: 9

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[(gamma
      glutamicacid)2]-[octadecanoyl])
<220> FEATURE:
<221> NAME/KEY: MOD_RES
```

<222> LOCATION: (16)
<223> OTHER INFORMATION: Xaa=aminoisobutyric acid

<400> SEQUENCE: 10

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-aminoethoxy)ethoxy)acetoyl)3]-[gamma
      glutamicacid]-[octadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 11

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys; Lys([Gly-Gly-Ser-Gly-Ser-
      Gly]-[gamma glutamic acid]-[octadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 12

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES

```
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 13

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Leu Arg Ala Lys
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[17-aminocarbonylheptadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 14

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: Lactam bridge bewteen the side chains at
      positions 16 and 20

<400> SEQUENCE: 15

His Xaa Gln Gly Thr Phe Thr Ser Asp Xaa Ser Lys Tyr Leu Asp Glu
1               5                   10                  15
```

```
Arg Arg Ala Lys Asp Phe Val Gln Trp Leu Met Asn Thr Lys
        20                  25                  30
```

<210> SEQ ID NO 16
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (16)
<223> OTHER INFORMATION: Xaa=modified Lys;
      Lys([(2-(2-(2-aminoethoxy)ethoxy)acetoyl)2]-[gamma
      glutamicacid]-[octadecanoyl])

<400> SEQUENCE: 16

```
His Xaa Gln Gly Thr Phe Thr Ser Asp Tyr Ser Lys Tyr Leu Asp Xaa
1               5                   10                  15

Arg Arg Ala Gln Asp Phe Val Gln Trp Leu Met Asn Thr Lys
        20                  25                  30
```

<210> SEQ ID NO 17
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (16)
<223> OTHER INFORMATION: Xaa=aminoisobutyric acid
<220> FEATURE:
<221> NAME/KEY: MOD_RES
<222> LOCATION: (20)
<223> OTHER INFORMATION: Xaa=modified Lys;
      Lys([(2-(2-(2-aminoethoxy)ethoxy)acetoyl)2]-[gamma
      glutamicacid]-[octadecanoyl])

<400> SEQUENCE: 17

```
His Xaa Gln Gly Thr Phe Thr Ser Asp Tyr Ser Lys Tyr Leu Asp Xaa
1               5                   10                  15

Arg Arg Ala Xaa Asp Phe Val Gln Trp Leu Met Asn Thr Lys
        20                  25                  30
```

<210> SEQ ID NO 18
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)]-[gamma glutamic
      acid]-[octadecanoyl])
<220> FEATURE:
<221> NAME/KEY: MOD_RES
<222> LOCATION: (16)

<223> OTHER INFORMATION: Xaa=aminoisobutyric acid

<400> SEQUENCE: 18

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
    Lys([(2-(2-(2-aminoethoxy)ethoxy)acetoyl)4]-[gamma
    glutamicacid]-[octadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 19

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
    Lys([(2-(2-(2-aminoethoxy)ethoxy)acetoyl)2]-[gamma
    glutamicacid]-[octadecanoyl])
<220> FEATURE:
<221> NAME/KEY: MOD_RES
<222> LOCATION: (16)..(20)
<223> OTHER INFORMATION: Lactam bridge bewteen the side chains at
    positions 16 and 20
<220> FEATURE:
<221> NAME/KEY: MOD_RES
<222> LOCATION: (30)
<223> OTHER INFORMATION: AMIDATION, C-terminal amidation

<400> SEQUENCE: 20

His Xaa Gln Gly Thr Phe Thr Ser Asp Xaa Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 21
<211> LENGTH: 30
<212> TYPE: PRT

```
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)3]-[gamma
      glutamicacid]-[octadecanoyl])
<220> FEATURE:
<221> NAME/KEY: MOD_RES
<222> LOCATION: (16)..(20)
<223> OTHER INFORMATION: Lactam bridge bewteen the side chains at
      positions 16 and 20

<400> SEQUENCE: 21

His Xaa Gln Gly Thr Phe Thr Ser Asp Xaa Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: Lactam bridge bewteen the side chains at
      positions 16 and 20

<400> SEQUENCE: 22

His Xaa Gln Gly Thr Phe Thr Ser Asp Xaa Ser Lys Tyr Leu Asp Lys
1               5                   10                  15

Arg Arg Ala Glu Asp Phe Val Gln Trp Leu Met Asn Thr Lys
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: 1,3-phenylenedimethyl cross linking between 16
``` and 20

<400> SEQUENCE: 23

His Xaa Gln Gly Thr Phe Thr Ser Asp Xaa Ser Lys Tyr Leu Asp Cys
1               5                   10                  15

Arg Arg Ala Cys Asp Phe Val Gln Trp Leu Met Asn Thr Lys
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
    Lys([(2-(2-(2-aminoethoxy)ethoxy)acetoyl)2]-[gamma
    glutamicacid]-[octadecanoyl])
<220> FEATURE:
<221> NAME/KEY: MOD_RES
<222> LOCATION: (16)..(20)
<223> OTHER INFORMATION: 1,4-piperazinyl cross linking between 16 and 20

<400> SEQUENCE: 24

His Xaa Gln Gly Thr Phe Thr Ser Asp Xaa Ser Lys Tyr Leu Asp Glu
1               5                   10                  15

Arg Arg Ala Glu Asp Phe Val Gln Trp Leu Met Asn Thr Lys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
    Lys([(2-(2-(2-aminoethoxy)ethoxy)acetoyl)4]-[gamma
    glutamicacid]-[octadecanoyl])
<220> FEATURE:
<221> NAME/KEY: MOD_RES
<222> LOCATION: (16)..(20)
<223> OTHER INFORMATION: Lactam bridge bewteen the side chains at
    positions 16 and 20
<220> FEATURE:
<221> NAME/KEY: MOD_RES
<222> LOCATION: (30)
<223> OTHER INFORMATION: AMIDATION, C-terminal amidation

<400> SEQUENCE: 25

His Xaa Gln Gly Thr Phe Thr Ser Asp Xaa Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 26
<211> LENGTH: 30
<212> TYPE: PRT

```
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)4]-[gamma
      glutamicacid]-[octadecanoyl])
<220> FEATURE:
<221> NAME/KEY: MOD_RES
<222> LOCATION: (16)..(20)
<223> OTHER INFORMATION: Lactam bridge bewteen the side chains at
      positions 16 and 20

<400> SEQUENCE: 26

His Xaa Gln Gly Thr Phe Thr Ser Asp Xaa Ser Lys Tyr Leu Asp Glu
1               5                   10                  15
Arg Arg Ala Lys Asp Phe Val Gln Trp Leu Met Asn Thr Lys
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: Lactam bridge bewteen the side chains at
      positions 16 and 20

<400> SEQUENCE: 27

His Xaa Gln Gly Thr Phe Thr Ser Asp Xaa Ser Lys Tyr Leu Asp Asp
1               5                   10                  15
Arg Arg Ala Lys Asp Phe Val Gln Trp Leu Met Asn Thr Lys
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: Lactam bridge bewteen the side chains at
``` positions 16 and 20

<400> SEQUENCE: 28

His Xaa Gln Gly Thr Phe Thr Ser Asp Xaa Ser Lys Tyr Leu Asp Lys
1               5                   10                  15

Arg Arg Ala Asp Asp Phe Val Gln Trp Leu Met Asn Thr Lys
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: di-sulfide bridge bewteen the side chains at
      positions 16 and 20

<400> SEQUENCE: 29

His Xaa Gln Gly Thr Phe Thr Ser Asp Xaa Ser Lys Tyr Leu Asp Cys
1               5                   10                  15

Arg Arg Ala Cys Asp Phe Val Gln Trp Leu Met Asn Thr Lys
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: 1,4-phenylenediamino cross linking between 16
      and 20

<400> SEQUENCE: 30

His Xaa Gln Gly Thr Phe Thr Ser Asp Xaa Ser Lys Tyr Leu Asp Glu
1               5                   10                  15

Arg Arg Ala Glu Asp Phe Val Gln Trp Leu Met Asn Thr Lys
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: oxyntomodulin analogue

```
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: 1,2-ethylenediamino cross linking between 16
      and 20

<400> SEQUENCE: 31

His Xaa Gln Gly Thr Phe Thr Ser Asp Xaa Ser Lys Tyr Leu Asp Glu
1               5                   10                  15

Arg Arg Ala Glu Asp Phe Val Gln Trp Leu Met Asn Thr Lys
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: 1,4-phenylenebiscarbonyl cross linking between
      16 and 20

<400> SEQUENCE: 32

His Xaa Gln Gly Thr Phe Thr Ser Asp Xaa Ser Lys Tyr Leu Asp Lys
1               5                   10                  15

Arg Arg Ala Lys Asp Phe Val Gln Trp Leu Met Asn Thr Lys
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: 4-carbonylpiperidin-1-yl cross linking between
      16 and 20

<400> SEQUENCE: 33
```

His Xaa Gln Gly Thr Phe Thr Ser Asp Xaa Ser Lys Tyr Leu Asp Lys
1               5                   10                  15

Arg Arg Ala Glu Asp Phe Val Gln Trp Leu Met Asn Thr Lys
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: 1-aminocyclohexan-4-carbonyl cross linking
      between 16 and 20

<400> SEQUENCE: 34

His Xaa Gln Gly Thr Phe Thr Ser Asp Xaa Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: 4-aminobenzoyl cross linking between 16 and 20

<400> SEQUENCE: 35

His Xaa Gln Gly Thr Phe Thr Ser Asp Xaa Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid

```
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: glycine cross linking between 16 and 20

<400> SEQUENCE: 36

His Xaa Gln Gly Thr Phe Thr Ser Asp Xaa Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: leucine cross linking between 16 and 20

<400> SEQUENCE: 37

His Xaa Gln Gly Thr Phe Thr Ser Asp Xaa Ser Lys Tyr Leu Asp Glu
1               5                   10                  15

Arg Arg Ala Lys Asp Phe Val Gln Trp Leu Met Asn Thr Lys
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: glycine cross linking between 16 and 20

<400> SEQUENCE: 38

His Xaa Gln Gly Thr Phe Thr Ser Asp Xaa Ser Lys Tyr Leu Asp Asp
1               5                   10                  15

Arg Arg Ala Lys Asp Phe Val Gln Trp Leu Met Asn Thr Lys
            20                  25                  30
```

```
<210> SEQ ID NO 39
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gamma
      glutamicacid]-[octadecanoyl])
<220> FEATURE:
<221> NAME/KEY: MOD_RES
<222> LOCATION: (16)..(20)
<223> OTHER INFORMATION: leucine cross linking between 16 and 20

<400> SEQUENCE: 39

His Xaa Gln Gly Thr Phe Thr Ser Asp Xaa Ser Lys Tyr Leu Asp Asp
1               5                   10                  15

Arg Arg Ala Lys Asp Phe Val Gln Trp Leu Met Asn Thr Lys
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (16)
<223> OTHER INFORMATION: Xaa=aminoisobutyric acid

<400> SEQUENCE: 40

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (9)
<223> OTHER INFORMATION: aa=modified Lys;
      Lys([(2-(2-(2-aminoethoxy)ethoxy)acetoyl)2]-[gammaglutamicacid]-
      [octadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 41

His Xaa Gln Gly Thr Phe Thr Ser Xaa Tyr Ser Lys Tyr Leu Asp Xaa
```

```
                1               5                   10                  15
Arg Arg Ala Gln Asp Phe Val Gln Trp Leu Met Asn Thr Lys
                20                  25                  30

<210> SEQ ID NO 42
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (30)
<223> OTHER INFORMATION: Xaa=modified Lys;
      Lys([(2-(2-(2-aminoethoxy)ethoxy)acetoyl)2]-[gammaglutamicacid]-
      [octadecanoyl])

<400> SEQUENCE: 42

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Xaa
                20                  25                  30

<210> SEQ ID NO 43
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gammaglutamicacid]-
      [15-carboxypentadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 43

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
                20                  25                  30

<210> SEQ ID NO 44
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gammaglutamicacid]-
      [17-carboxyheptadecanoyl])
<220> FEATURE:
<221> NAME/KEY: MOD_RES
<222> LOCATION: (16)
<223> OTHER INFORMATION: Xaa=aminoisobutyric acid
```

```
<400> SEQUENCE: 44

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gammaglutamicacid]-
      [19-carboxynonadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 45

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gammaglutamicacid]-
      [15-(N-(carboxymethyl)amino)carbonylpentadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 46

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
```

```
<220> FEATURE:
<221> NAME/KEY: MOD_RES
<222> LOCATION: (10)
<223> OTHER INFORMATION: Xaa=modified Lys;
      Lys([(2-(2-(2-aminoethoxy)ethoxy)acetoyl)2]-[gammaglutamicacid]-
      [15-(N-(1S)-(1-carboxy-2-
      methylpropyl)amino)carbonylpentadecanoyl])
<220> FEATURE:
<221> NAME/KEY: MOD_RES
<222> LOCATION: (16)
<223> OTHER INFORMATION: Xaa=aminoisobutyric acid

<400> SEQUENCE: 47

His Xaa Gln Gly Thr Phe Thr Ser Asp Xaa Ser Lys Tyr Leu Asp Xaa
1               5                   10                  15

Arg Arg Ala Gln Asp Phe Val Gln Trp Leu Met Asn Thr Lys
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: oxyntomodulin analogue
<220> FEATURE:
<221> NAME/KEY: MOD_RES
<222> LOCATION: (2)
<223> OTHER INFORMATION: Xaa=aminoisobutyric acid
<220> FEATURE:
<221> NAME/KEY: MOD_RES
<222> LOCATION: (16)..(20)
<223> OTHER INFORMATION: Lactam bridge bewteen the side chains at
      positions 16 and 20

<400> SEQUENCE: 48

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Lys Cys
            20                  25                  30

<210> SEQ ID NO 49
<211> LENGTH: 38
<212> TYPE: PRT
<213> ORGANISM: Artificial Sequence
<220> FEATURE:
<223> OTHER INFORMATION: oxyntomodulin analogue
<220> FEATURE:
<221> NAME/KEY: VARIANT
<222> LOCATION: (2)
<223> OTHER INFORMATION: Xaa=Ser or aminoisobutyric acid
<220> FEATURE:
<221> NAME/KEY: VARIANT
<222> LOCATION: (9)
<223> OTHER INFORMATION: Xaa=Asp or modified Lys
<220> FEATURE:
<221> NAME/KEY: VARIANT
<222> LOCATION: (10)
<223> OTHER INFORMATION: Xaa=Tyr or modified Lys
<220> FEATURE:
<221> NAME/KEY: VARIANT
<222> LOCATION: (11)
<223> OTHER INFORMATION: Xaa=Ser or modified Lys
<220> FEATURE:
<221> NAME/KEY: VARIANT
<222> LOCATION: (12)
<223> OTHER INFORMATION: Xaa=Lys or modified Lys
<220> FEATURE:
<221> NAME/KEY: VARIANT
<222> LOCATION: (13)
<223> OTHER INFORMATION: Xaa=Tyr or modified Lys
<220> FEATURE:
<221> NAME/KEY: VARIANT
<222> LOCATION: (14)
```

```
<223> OTHER INFORMATION: Xaa=Leu or modified Lys
<220> FEATURE:
<221> NAME/KEY: VARIANT
<222> LOCATION: (15)
<223> OTHER INFORMATION: Xaa=Asp or modified Lys
<220> FEATURE:
<221> NAME/KEY: VARIANT
<222> LOCATION: (16)
<223> OTHER INFORMATION: Xaa=Ser, aminoisobutyric acid or modified Lys
<220> FEATURE:
<221> NAME/KEY: VARIANT
<222> LOCATION: (20)
<223> OTHER INFORMATION: Xaa=Gln or modified Lys
<220> FEATURE:
<221> NAME/KEY: VARIANT
<222> LOCATION: (27)
<223> OTHER INFORMATION: Xaa=Met or Leu
<220> FEATURE:
<221> NAME/KEY: VARIANT
<222> LOCATION: (28)
<223> OTHER INFORMATION: Xaa=Asn or Arg
<220> FEATURE:
<221> NAME/KEY: VARIANT
<222> LOCATION: (29)
<223> OTHER INFORMATION: Xaa=Thr or Ala
<220> FEATURE:
<221> NAME/KEY: VARIANT
<222> LOCATION: (30)
<223> OTHER INFORMATION: Xaa=Lys or modified Lys
<220> FEATURE:
<221> NAME/KEY: VARIANT
<222> LOCATION: (31)..(37)
<223> OTHER INFORMATION: XaaXaaXaaXaaXaaXaaXaa at positions 31-37 are
      absent or RNRNNIA(ArgAsnArgAsnAsnIleAla)
<220> FEATURE:
<221> NAME/KEY: VARIANT
<222> LOCATION: (38)
<223> OTHER INFORMATION: Xaa=optional, when XaaXaaXaaXaaXaaXaaXaa at
      positions 31-37 is RNRNNIA(ArgAsnArgAsnAsnIleAla), Xaa at position
      38 is absent or is modified Lys

<400> SEQUENCE: 49

His Xaa Gln Gly Thr Phe Thr Ser Xaa Xaa Xaa Xaa Xaa Xaa Xaa
1               5                   10                  15

Arg Arg Ala Xaa Asp Phe Val Gln Trp Leu Xaa Xaa Xaa Xaa Xaa Xaa
            20                  25                  30

Xaa Xaa Xaa Xaa Xaa Xaa
        35

<210> SEQ ID NO 50
<211> LENGTH: 38
<212> TYPE: PRT
<213> ORGANISM: Artificial Sequence
<220> FEATURE:
<223> OTHER INFORMATION: oxyntomodulin analogue
<220> FEATURE:
<221> NAME/KEY: VARIANT
<222> LOCATION: (2)
<223> OTHER INFORMATION: Xaa=Ser or aminoisobutyric acid
<220> FEATURE:
<221> NAME/KEY: VARIANT
<222> LOCATION: (10)
<223> OTHER INFORMATION: Xaa=Tyr or modified Lys
<220> FEATURE:
<221> NAME/KEY: VARIANT
<222> LOCATION: (16)
<223> OTHER INFORMATION: Xaa=Ser, aminoisobutyric acid or modified Lys
<220> FEATURE:
<221> NAME/KEY: VARIANT
<222> LOCATION: (20)
<223> OTHER INFORMATION: Xaa=Gln or modified Lys
<220> FEATURE:
<221> NAME/KEY: VARIANT
<222> LOCATION: (27)
<223> OTHER INFORMATION: Xaa=Met or Leu
```

```
<220> FEATURE:
<221> NAME/KEY: VARIANT
<222> LOCATION: (28)
<223> OTHER INFORMATION: Xaa=Asn or Arg
<220> FEATURE:
<221> NAME/KEY: VARIANT
<222> LOCATION: (29)
<223> OTHER INFORMATION: Xaa=Thr or Ala
<220> FEATURE:
<221> NAME/KEY: VARIANT
<222> LOCATION: (30)
<223> OTHER INFORMATION: Xaa=Lys or modified Lys
<220> FEATURE:
<221> NAME/KEY: VARIANT
<222> LOCATION: (31)..(37)
<223> OTHER INFORMATION: XaaXaaXaaXaaXaaXaaXaa at positions 31-37 are
      absent or RNRNNIA(ArgAsnArgAsnAsnIleAla)
<220> FEATURE:
<221> NAME/KEY: VARIANT
<222> LOCATION: (38)
<223> OTHER INFORMATION: Xaa=optional, when XaaXaaXaaXaaXaaXaaXaa at
      positions 31-37 is RNRNNIA(ArgAsnArgAsnAsnIleAla), Xaa at position
      38 is absent or is modified Lys

<400> SEQUENCE: 50

His Xaa Gln Gly Thr Phe Thr Ser Asp Xaa Ser Lys Tyr Leu Asp Xaa
1               5                   10                  15

Arg Arg Ala Xaa Asp Phe Val Gln Trp Leu Xaa Xaa Xaa Xaa Xaa Xaa
            20                  25                  30

Xaa Xaa Xaa Xaa Xaa Xaa
        35

<210> SEQ ID NO 51
<211> LENGTH: 7
<212> TYPE: PRT
<213> ORGANISM: Artificial Sequence
<220> FEATURE:
<223> OTHER INFORMATION: oxyntomodulin peptide

<400> SEQUENCE: 51

Arg Asn Arg Asn Asn Ile Ala
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic construct

<400> SEQUENCE: 52

Gly Gly Ser Gly Ser Gly
1               5

<210> SEQ ID NO 53
<211> LENGTH: 30
<212> TYPE: PRT
<213> ORGANISM: Artificial Sequence
<220> FEATURE:
<223> OTHER INFORMATION: oxyntomodulin analogue
<220> FEATURE:
<221> NAME/KEY: VARIANT
<222> LOCATION: (2)
<223> OTHER INFORMATION: Xaa=Ser or aminoisobutyric acid
<220> FEATURE:
<221> NAME/KEY: VARIANT
<222> LOCATION: (10)
<223> OTHER INFORMATION: Xaa=modified Lys
<220> FEATURE:
<221> NAME/KEY: VARIANT
<222> LOCATION: (16)
```

```
<223> OTHER INFORMATION: Xaa=Asp, Glu, Cys, Hcy (Homocysteine), Lys or
      Orn (Ornithine)
<220> FEATURE:
<221> NAME/KEY: VARIANT
<222> LOCATION: (20)
<223> OTHER INFORMATION: Xaa=Asp, Glu, Cys, Hcy (Homocysteine), Lys or
      Orn (Ornithine)

<400> SEQUENCE: 53

His Xaa Gln Gly Thr Phe Thr Ser Asp Xaa Ser Lys Tyr Leu Asp Xaa
1               5                   10                  15

Arg Arg Ala Xaa Asp Phe Val Gln Trp Leu Met Asn Thr Lys
            20                  25                  30
```

ACYLATED OXYNTOMODULIN PEPTIDE ANALOG

CROSS REFERENCE TO RELATED APPLICATIONS

This application is a National Stage of International Application No. PCT/KR2018/009425 filed Aug. 16, 2018, claiming priority based on Korean Patent Application No. 10-2017-0103798 filed Aug. 16, 2017 and Korean Patent Application 10-2018-0095717 filed Aug. 16, 2018.

TECHNICAL FIELD

The present invention relates to oxyntomodulin peptide analogs and pharmaceutical composition comprising the same for the treatment or prevention of obesity, overweight, or non-insulin-dependent diabetes accompanying said conditions.

BACKGROUND ART

Metabolic diseases, or metabolic syndrome, are usually caused by abnormalities in the metabolism of glucose, fat, proteins, and others. The term refers to a various diseases caused by abnormalities in glucose and fat metabolism, including cancer, diabetes, bone metabolism disorders, fatty liver, obesity, and cardiovascular disease. According to the 2001 report of the National Cholesterol Education Program (NCEP) of the United States and 2012 publications of International Diabetes Federation (IDF), diagnosis of metabolic syndrome requires the presence of 3 or more of the following 5 factors: (1) abdominal obesity indicated by a waist circumference of 102 cm (NCEP) or 94 cm (IDF) for males and 88 cm (NCEP) or 80 cm (IDF) for females; (2) hypertriglyceridemia indicated by triglyceride level of 150 mg/dL or above; (3) HDL cholesterol level at or lower than 40 mg/dL (male) or 50 mg/dL (female); (4) hypertension indicated by a blood pressure of 130/85 mmHg or higher; (5) a fasting glucose level of 110 mg/dL or higher.

According to the World Health Organization (WHO), worldwide obesity rate has more than doubled from 1980 to 2014; 39% of adults aged 18 years or older (38% of male and 40% of female) were obese in 2014. Obesity and overweight is caused by energy imbalance between caloric intake and output, causes of which include increased consumption of foods with high fat content and high energy density and reduced physical activity due to modern work and lifestyle, changes in modes of transportation, and increased urbanization. Diabetes rate has also rapidly increased; 4.7% of adults aged 18 years or older had diabetes in 1980, compared to 8.5% in 2015. Diabetes rate is increasing more rapidly in middle class and low-income nations and is among major causes of blindness, renal failure, cardiac arrest, and strokes.

Glucagon is a hormone produced by alpha cells of the pancreas. It works to raise the concentration of glucose by stimulating gluconeogenesis and promoting the breakdown of glycogen stored in liver. When liver-stored glycogen becomes depleted, glucagon stimulates liver and kidney to synthesize new glucose. It is also known to affect appetite suppression and breaking down of triglyceride storage into fatty acids, causing increased metabolism, thereby affecting body weight loss (Diabetes.co.uk. the global diabetes community, Anim Sci J. 2016; 87(9): 1090-1098).

Glucagon-like peptide-1 (GLP-1), a glucagon derivative, is a peptide hormone which reduces blood glucose. GLP-1 is secreted in L-cells of the small intestine after food intake. It has a very short half-life of no longer than 2 minutes. It is reported that glucose increases secretion of GLP-1, which induces insulin secretion by pancreatic beta cells, ultimately controlling blood glucose level and improving beta cell functions. GLP-1 also suppresses secretion of glucagon, inhibits gastric emptying, and reduces food intake (Physiol Rev. 2007; 87(4):1409-1439). Novo Nordisk's liraglutide is human GLP-1 derivative which has been developed to treat type 2 diabetes and obesity indications and is to be injected once per day. Liraglutide is a long-acting GLP-1 receptor agonist which binds to the same receptors as endogenous GLP-1, stimulating insulin secretion, thereby modulating blood glucose level and reducing appetite, thus inhibiting body weight gain and reducing triglycerides. Liraglutide has been marketed in the U.S. and Europe as Victoza for type II diabetes and Saxenda for obesity (Expert Rev Cardiovasc Ther. 2015; 13(7):753-767). Exenatide, lixisenatide, albiglutide, and dulaglutide also have been developed for the treatment of diabetes. However, such GLP-1 receptor agonists are reported to cause side effects such as nausea, vomiting, appetite reduction, headache, constipation, and abdominal bloating (Korean J Med. 2014; 87(1):9-13).

Oxyntomodulin is a peptide derived from proglucagon, a precursor of glucagon. Oxyntomodulin consists of 37 amino acid peptides, including the complete 29 amino acids of glucagon, and is known to be a dual agonist that binds both to GLP-1 and glucagon receptors. It produces body weight loss effect by reducing food intake and increasing energy metabolism. Oxyntomodulin is known to be more effective than selective GLP-1 receptor agonists at lowering body weight. It has been reported that the risk of hyperglycemia caused by a rise in glucose due to glucagon receptor activation may be offset by insulin secretion of GLP-1 receptors. Oxyntomodulin has been reported to reduce food intake and body weight, and to improve energy expenditure and glucose metabolism in non-clinical testing (Diabetes. 2009; 58(10):2258-2266). In a clinical study, oxyntomodulin showed body weight loss effects of 2.3 kg on average when administered subcutaneously for 4 weeks, 3 times per day, to overweight and obese patients (Diabetes. 2005; 54:2390-2395). It has been shown to produce significant insulin secretion and blood glucose lowering effects against placebo (Diabetes. 2013; 62(Suppl. 1):A48). In another clinical study, oxyntomodulin reduced energy intake without side effects such as vomiting or appetite stimulation from continual use of oxyntomodulin (J Clin Endocrinol Metab. 2003; 88:4696-4701). Oxyntomodulin's effectiveness at glycemic control, lowering of food intake, and satiety promotion have garnered interests in its potential as a new method of obesity treatment and glycemic control (Molecular metabolism. 2014; 3:241-251). However, because oxyntomodulin, like GLP-1, can be cleaved by dipeptidyl peptidase-IV (DPP-IV), it is unstable in vivo and has a very short in vivo half-life (J Biol Chem. 2003; 278: 22418-22423).

Therefore, studies are being conducted on DPP-IV resistant oxyntomodulin derivatives that make oxyntomodulin's pharmacological and treatment effects long-lasting by binding to GLP-1 and glucagon receptors in balanced and selective ways and overcome the side effects of each hormone peptide (Diabetes. 2009; 58(10):2258-2266). Many pharmaceutical manufacturers including Merck, Zealand, MedImmune, and Hanmi Pharmaceutical are working on development of lead compounds.

Against this background, the present inventors have worked to solve the problem described above, culminating in the present invention, which relates to a pharmaceutical composition for the treatment of obesity or obesity-accompanying diabetes by developing a synthetic oxyntomodulin peptide analog with (1) DPP-IV resistance, (2) optimized metabolic stability of acylation, and (3) improved action compared to the original oxyntomodulin on GLP-1 and glucagon receptors.

DETAILED DESCRIPTION OF THE INVENTION

Technical Problem

The object of the present invention is to provide an oxyntomodulin peptide analog with higher activity against GLP-1 and glucagon receptors than oxyntomodulin and higher in vivo half-life from improved chemical stability by acylation (Molecular metabolism 2013; 2:468-479), and pharmaceutical compositions comprising said analog to be used in treating and preventing conditions caused by or characterized by obesity, overweight, or non-insulin-dependent diabetes.

Solution to Problem

As a solution to the above-mentioned problem, the present invention provides a novel peptide comprising the amino acid sequence of Chemical Formula I below, which is an oxyntomodulin peptide analog.

```
<Chemical Formula I>
                                    (SEQ ID NO: 49)
His-X1-Gln-Gly-Thr-Phe-Thr-Ser-X2-X3-X4-X5-X6-X7-

X8-X9-Arg-Arg-Ala-X10-Asp-Phe-Val-Gln-Trp-Leu-X11-

X12-X13-X14-X15-X16
```

In the formula above,
$X_1$ is Ser or Aib (aminoisobutyric acid);
$X_2$ is Asp or Z;
$X_3$ is Tyr or Z;
$X_4$ is Ser or Z;
$X_5$ is Lys or Z;
$X_6$ is Tyr or Z;
$X_7$ is Leu or Z;
$X_8$ is Asp or Z;
$X_9$ is Ser, Aib (aminoisobutyric acid) or Z;
$X_{10}$ is Gln or Z;
$X_{11}$ is Met or Leu;
$X_{12}$ is Asn or Arg;
$X_{13}$ is Thr or Ala;
$X_{14}$ is Lys or Z;
$X_{15}$ is RNRNNIA (SEQ ID NO:51) or absent;
$X_{16}$ is Z or absent, if $X_{15}$ exists;
the C-terminal amino acid may be amidated arbitrarily;
at least one or more of $X_2$, $X_3$, $X_4$, $X_5$, $X_6$, $X_7$, $X_8$, $X_9$, $X_{10}$, $X_{14}$ and $X_{16}$ is Z;
Z is modified form of Lys, attached at whose side chains are a polymeric moiety and spacer conjugate ("$Z_1$") and a lipophilic lipid moiety ("$Z_2$"); where $Z_1$ is directly attached to Lys side chain via acyl functional group; and $Z_2$ is attached to Lys side chain via $Z_1$; and $Z_1$ is Structural Formula (1) or (2) below; and

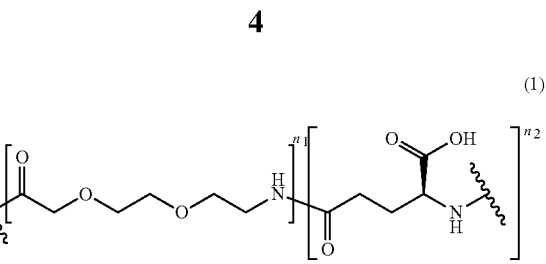

$n_1 = 1\sim4$
$n_2 = 1\sim2$

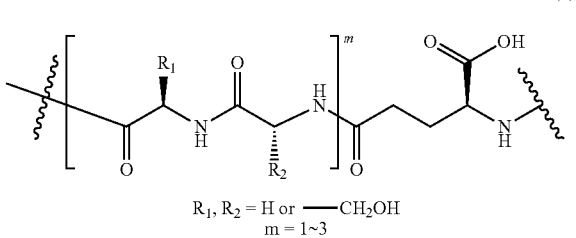

$R_1, R_2 = H$ or $—CH_2OH$
$m = 1\sim3$

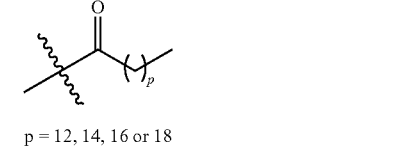

$p = 12, 14, 16$ or $18$

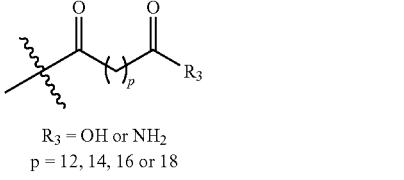

$R_3 = OH$ or $NH_2$
$p = 12, 14, 16$ or $18$ $Z_2$ is Structural Formula (3) or (4) below.

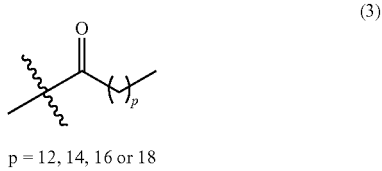

$p = 12, 14, 16$ or $18$

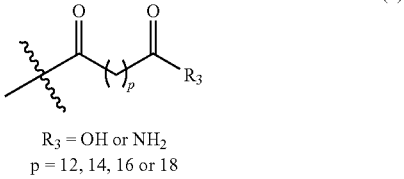

$R_3 = OH$ or $NH_2$
$p = 12, 14, 16$ or $18$

In the present invention, the following three-letter and/or single-letter abbreviations are used to refer to specific amino acids:
Ala(A), Lys(K), Asn(N), Asp(D), Cys(C), His(H), Ile(I), Met(M), Ser(S), Val(V), Gly(G), Leu(L), Pro(P), Thr(T), Phe(F), Arg(R), Tyr(Y), Trp(W), Glu(E), Gln(Q), Aib(aminoisobutyric acid).

In the present invention, "oxyntomodulin" refers to the peptide made from pre-glucagon, the precursor to glucagon. Naturally-occurring oxyntomodulin has the following amino acid sequence: HSQGTFTSDYSKYLDSR-RAQDFVQWLMNTKRNRNNIA (SEQ ID NO:1).

$Z_1$, which is one of the components of Z in the present invention, may be in the form of a copolymer having polyethylene glycol as polymeric moiety, ethylene glycol as monomer, ethanolamine, and lactic acid; or, a poly-amino acid copolymer comprising glycine and serine as monomers. The poly-amino acid may be of the amino acid sequence GGSGSG (SEQ ID NO: 52). The chemical compound of the present invention may comprise two or more repeating units of the above-mentioned polymeric moiety.

Furthermore, $Z_1$ may have a functional group at one terminal end to be attached to any residue or side chain of the above-mentioned oxyntomodulin peptide analog. Preferably, it is an acyl group, in which case it may be attached to the amino group of side chain via an amide bond.

In some embodiment examples, $Z_1$ may have a functional group at one terminus to bond to a spacer. Preferably, it is amino group, in which case it may form an amide bond to the spacer's carboxy group. Preferably, $Z_1$ is water soluble and thus may be amphiphilic or hydrophilic.

A spacer in the present invention is L-glutamic acid residue, whose γ-carboxylic acid is covalently bonded to $Z_1$ (polymeric moiety) and whose α-amino group may be covalently bonded to $Z_2$ (lipophilic lipid moiety), and it may have 2 or more repeating units.

The $Z_2$ lipid moiety, which is another component of Z, directly attaches to the spacer. The spacer directly attaches to the polymeric moiety. The polymeric moiety may directly attach to the side chain of amino acid residue on $X_2$, $X_3$, $X_4$, $X_5$, $X_6$, $X_7$, $X_8$, $X_9$, $X_{10}$, $X_{14}$ or $X_{16}$ of the oxyntomodulin peptide analog of the present invention. Preferably, Lys may be used as the amino acid residue that enables this attachment.

Furthermore, $Z_2$ comprises $C_{14}$-$C_{20}$ saturated hydrocarbon chain, whose terminal carbon is in the form of carboxylic acid, primary amide, or carboxylic acid covalently bonded to any single amino acid. In this case, the hydrocarbon chain may be branched or linear. The functional group needed for the hydrocarbon chain to attach to the spacer forms part of the above-mentioned lipid moiety and may comprise acyl, sulfonyl, N atom, O atom, S atom, or the likes.

Therefore, the spacer may be attached by ester, sulfonyl ester, thioester, amide or sulfonamide. Preferably, the hydrocarbon chain is attached to the amino group of the spacer in the form of an amide bond via acyl group; therefore, the hydrocarbon chain may be part of alkanoyl group form in particular.

While no limitation of the scope of interpretation to a particular theory is intended, the mechanism of improved in vivo half-life of the present invention is believed to involve its lipophilic lipid moiety bonding to albumin in the bloodstream, preventing the compound of the present invention from reacting as a substrate for various lyases in the bloodstream.

In the present invention, one or more amino acid side chains of the oxyntomodulin peptide analog is attached to lipophilic lipid moiety via polymeric moiety and spacer. Such chemical modification can induce pharmaceutically beneficial effects such as increasing in vivo availability and/or half-life and/or increasing bioavailability of oxyntomodulin peptide analog of the present invention.

A novel peptide comprising the amino acid sequence of Chemical Formula I above may be prepared by taking naturally-occurring oxyntomodulin and substituting Ser residue at position 2 with Aib. In this example of the present invention, Aib is introduced to the $X_1$ position of the oxyntomodulin peptide analog. This compound is thought to be more resistant to dipeptidyl peptidase IV than naturally-occurring oxyntomodulin. Ultimately, the oxyntomodulin peptide analog of the present invention shows improved in vivo stability compared to naturally-occurring oxyntomodulin.

Also, above-mentioned acylated oxyntomodulin peptide analog of the present invention may be prepared by substituting Met residue of natural oxyntomodulin with Leu at position 27, Asn with Arg at position 28, and Thr with Ala at position 29. For example, Compound 12 (SEQ ID NO: 13) of the examples below is prepared by substituting $X_{11}$ with Leu, $X_{12}$ with Arg, and $X_{13}$ with Ala.

In the present invention, preferable oxyntomodulin peptide analog is a novel peptide comprising the amino acid sequence of Chemical Formula I-1 below.

```
<Chemical Formula I-1>
                                    (SEQ ID NO: 50)
HX₁QGTFTSDX₃SKYLDX₉RRAX₁₀DFVQWLX₁₁X₁₂X₁₃X₁₄X₁₅X₁₆
```

In the above amino acid sequence, $X_1$ is Ser or Aib (aminoisobutyric acid);

$X_3$ is Tyr or Z;

$X_9$ is Ser, Aib or Z;

$X_{10}$ is Gln or Z;

$X_{11}$ is Met or Leu;

$X_{12}$ is Asn or Arg;

$X_{13}$ is Thr or Ala;

$X_{14}$ is Lys or Z;

$X_{15}$ is RNRNNIA (SEQ ID NO: 51) or absent;

If $X_{15}$ exists, $X_{16}$ is Z or absent, and C-terminal may be amidated; and Z is as defined in Chemical Formula I above.

Embodiment examples comprising peptide analogs of Chemical Formula I above include, but are not limited to, Compound 1 (SEQ ID NO: 2), Compound 2 (SEQ ID NO: 3), Compound 3 (SEQ ID NO: 4), Compound 4 (SEQ ID NO: 5), Compound 5 (SEQ ID NO: 6), Compound 6 (SEQ ID NO: 7), Compound 7 (SEQ ID NO: 8), Compound 8 (SEQ ID NO: 9), Compound 9 (SEQ ID NO: 10), Compound 10 (SEQ ID NO: 11), Compound 11 (SEQ ID NO: 12), Compound 12 (SEQ ID NO: 13), Compound 13 (SEQ ID NO: 14), Compound 15 (SEQ ID NO: 16), Compound 16 (SEQ ID NO: 17), Compound 17 (SEQ ID NO: 18), and Compound 18 (SEQ ID NO: 19).

Also, oxyntomodulin peptide analog of the above-mentioned Chemical Formula I according to the present invention may have within its amino acid sequence one or more intramolecular cross-link(s); i.e., $X_9$ and $X_{10}$ may form a cyclic peptide via intramolecular bonding (lactamization, di-sulfide bond) or via a cross-linker.

Therefore, another object of the present invention is to provide a novel oxyntomodulin peptide analog comprising the amino acid sequence of Chemical Formula II below.

```
<Chemical Formula II>
                                    (SEQ ID NO: 53)
His-X₁₇-Gln-Gly-Thr-Phe-Thr-Ser-Asp-X₁₈-Ser-Lys- Tyr-Leu-Asp-X₁₉-Arg-Arg-Ala-X₂₀-Asp-Phe-Val-Gln- Trp-Leu-Met-Asn-Thr-Lys
```

In the formula above, $X_{17}$ is Ser or Aib (Aminoisobutric acid);

$X_{18}$ is Z;

$X_{19}$ is Asp, Glu, Cys, Hcy (Homocysteine), Lys or Orn (Ornithine);

$X_{20}$ is Asp, Glu, Cys, Hcy (Homocysteine), Lys or Orn (Ornithine);

$X_{19}$ and $X_{20}$ may form a cyclic peptide via intramolecular bond or cross-linker, in which case, the cyclic peptide has either a lactam ring formed by an amide bond between two residues, a di-sulfide ring formed by a di-sulfide bond between two residues, or a cross-linked ring formed by a cross-linker bond between two residues;

C-terminal amino acid may optionally be amidated;

Z is modified form of Lys, at whose side chain polymeric moiety and spacer assembly ("$Z_1$") and lipophilic lipid moiety ("$Z_2$") are attached, where $Z_1$ is directly attached to Lys side chain via acyl functional group, and $Z_2$ is attached to Lys side chain via $Z_1$, and $Z_1$ is Structural Formula (1) or (2) below; and

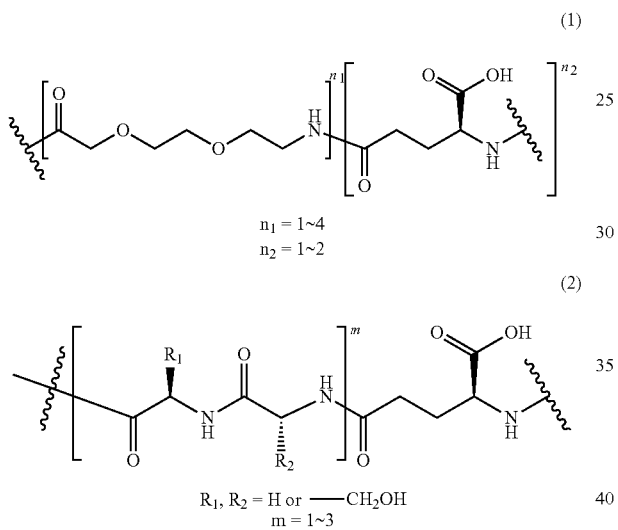

$Z_2$ is Structural Formula (3) or (4) below.

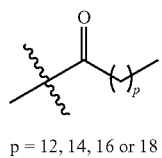

p = 12, 14, 16 or 18

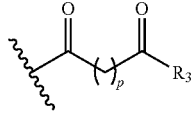

$R_3$ = OH or $NH_2$
p = 12, 14, 16 or 18

The intramolecular bond between $X_{19}$ and $X_{20}$ is intramolecular lactam ring formation bond if $X_{19}$ and $X_{20}$ are Asp (or Glu) and Lys (or Orn) respectively or Lys (or Orn) and Asp (or Glu) respectively, or intramolecular di-sulfide ring formation bond if $X_{19}$ and $X_{20}$ are Cys (or Hcy) and Cys (or Hcy);

When $X_{19}$ and $X_{20}$ are Cys (or Hcy) and Cys (or Hcy) respectively, the cross-linker forms a ring by bonding to the thiol functional group at both Cys (or Hcy) side chains, in which case, the cross-linker is $C_1$-$C_6$ linear or branched chain alkyl, $C_3$-$C_8$ saturated or unsaturated cycloalkyl, $C_6$-$C_{10}$ aryl, or $C_5$-$C_{12}$ heteroaryl or fused heterocyclic aryl; preferably, it is:

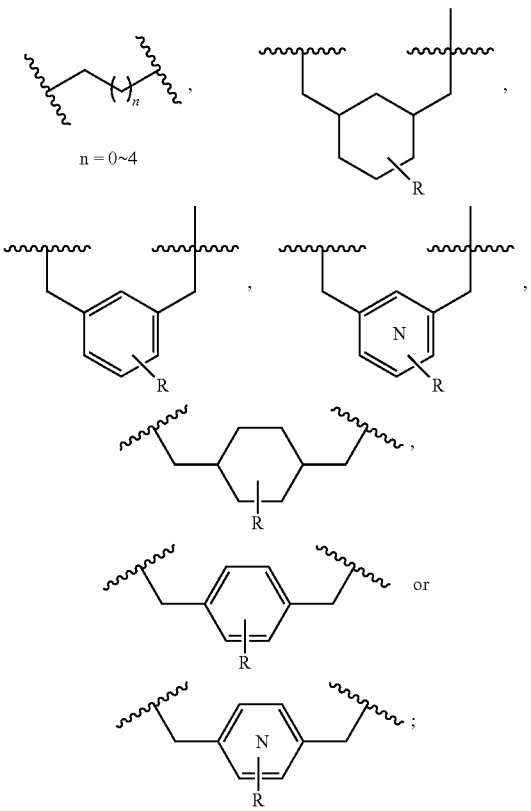

R is hydrogen or $C_1$-$C_6$ linear or branched alkyl chain;

When $X_{19}$ and $X_{20}$ are Asp (or Glu) and Asp (or Glu) respectively, the cross-linker forms a ring by an amide bond to the carboxyl group of both Asp (or Glu) side chains, in which case, the cross-linker is di-amino $C_1$-$C_6$ linear or branched chain alkyl, di-amino $C_3$-$C_8$ saturated or unsaturated cycloalkyl, aminopiperidine, piperazine, di-amino $C_6$-$C_{10}$ aryl, or di-amino $C_5$-$C_{12}$ heteroaryl or fused heterocyclic aryl; and preferably, it is:

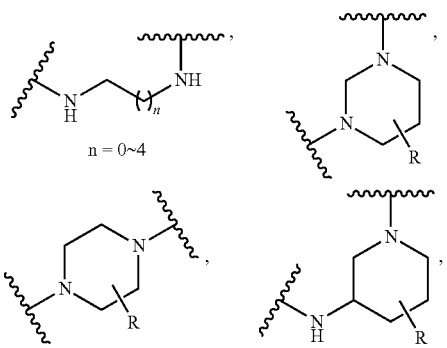

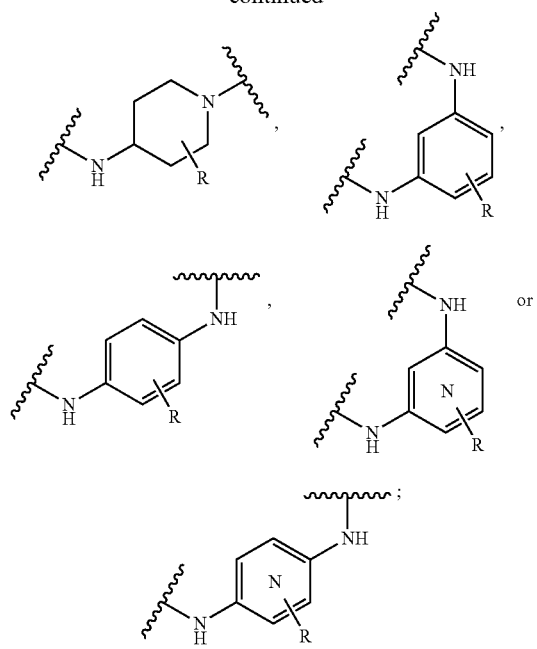

R is hydrogen or $C_1$-$C_6$ linear or branched alkyl;

When $X_{19}$ and $X_{20}$ are Lys (or Orn) Lys (or Orn) respectively, the cross-linker forms a ring by an amide bond to the amine group at both Lys (or Orn) side chains, in which case, the cross-linker is di-carbonyl $C_1$-$C_6$ linear or branched chain alkyl, di-carbonyl $C_3$-$C_8$ saturated or unsaturated cycloalkyl, di-carbonyl $C_6$-$C_{10}$ aryl or di-carbonyl $C_5$-$C_{12}$ heteroaryl or fused heterocyclic aryl, and preferably, it is:

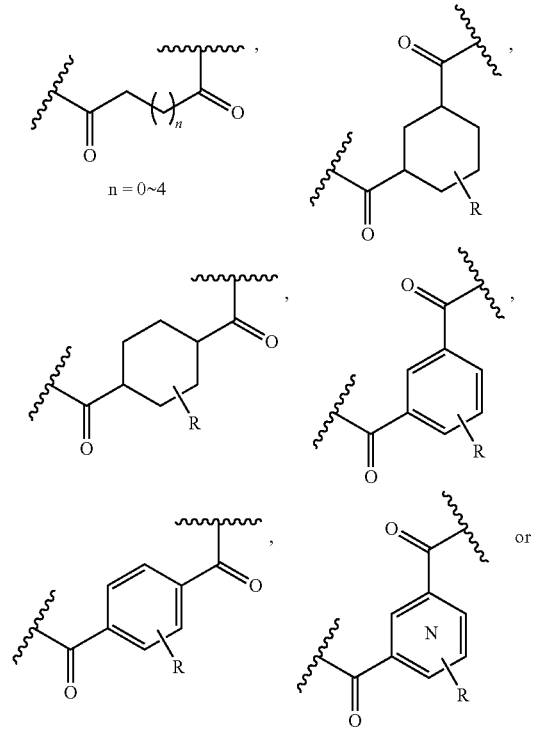

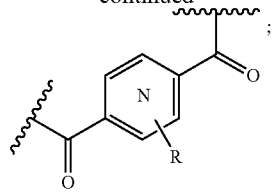

R is hydrogen or $C_1$-$C_6$ linear or branched chain alkyl;

When $X_{19}$ and $X_{20}$ are Asp (or Glu) and Lys (or Orn) respectively, or Lys (or Orn) and Asp (or Glu) respectively, the cross-linker links Asp (or Glu) by amide bond between the carboxyl group of the Asp (or Glu) side chain and amine functional group of the cross-linker; the amine group of the Lys (or Orn) side chain forms an amide bond with the carboxyl functional group of the cross-linker to form a ring; in this case, the cross-linker is alpha amino acids (such as Gly, Val, Leu, Ile), beta amino acids, carbonyl $C_1$-$C_6$ linear or branched chain alkylamine, carbonyl $C_3$-$C_8$ saturated or unsaturated alkylamine, carbonyl piperidine, aminobenzoyl, carbonyl $C_6$-$C_{10}$ arylamine or carbonyl $C_5$-$C_{12}$ heteroarylamine or fused heterocyclic arylamine; and preferably, it is:

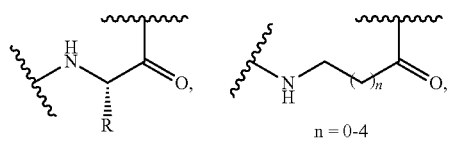

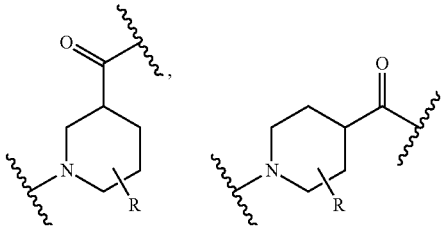

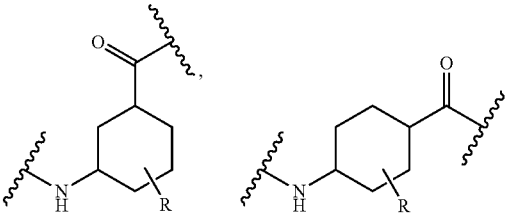

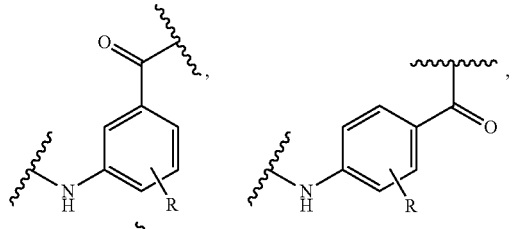

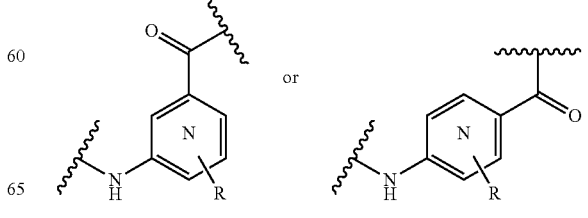

and

R is hydrogen or $C_1$-$C_6$ linear or branched chain alkyl.

Embodiment examples comprising the peptide analog of Chemical Formula II comprising one or more intramolecular cross-link(s) within the amino acid sequence of Chemical Formula I above includes, but are not limited to, Compound 14 (SEQ ID NO: 15), Compound 19 (SEQ ID NO: 20), Compound 20 (SEQ ID NO: 21), Compound 21 (SEQ ID NO: 22), Compound 22 (SEQ ID NO: 23), Compound 23 (SEQ ID NO: 24), Compound 24 (SEQ ID NO: 25), Compound 25 (SEQ ID NO: 26), Compound 27 (SEQ ID NO: 28), Compound 28 (SEQ ID NO: 29), Compound 29 (SEQ ID NO: 30), Compound 30 (SEQ ID NO: 31), Compound 31 (SEQ ID NO: 32), Compound 32 (SEQ ID NO: 33), Compound 33 (SEQ ID NO: 34), Compound 34 (SEQ ID NO: 35), Compound 35 (SEQ ID NO: 36), Compound 36 (SEQ ID NO: 37), Compound 37 (SEQ ID NO: 38), and Compound 38 (SEQ ID NO: 39).

The cross-linking of the peptide of the above Chemical Formula II may form as a chemical covalent bond or an interionic interaction within residues in each of any two amino acids spaced 3 amino acids apart in the sequence of Chemical Formula I or between any functional groups within side chain. Preferably, the cross-linking may be amino acid side chains of $X_{19}$ residue and $X_{20}$ residue forming a lactone ring, lactam ring, or di-sulfide ring; or, it may be amino acid side chains of $X_{19}$ residue and $X_{20}$ residue linking to a cross-linker, forming a ring.

A novel peptide comprising the amino acid sequence of the above-mentioned Chemical Formula II may be prepared by taking a naturally-occurring oxyntomodulin and substituting the Ser residue at position 16 with either Cys or Hcy; substituting the Gln residue at position 20 with Cys or Hcy; and forming inter-molecular di-sulfide ring. For example, Compound 28 (SEQ ID NO: 29), one of the embodiment examples below, is prepared by substituting $X_{19}$ with Cys, substituting $X_{20}$ with Cys, and forming a di-sulfide ring within the molecule.

Also, the above-mentioned acylated oxyntomodulin peptide analog according to the present invention may be prepared by taking a naturally-occurring oxyntomodulin and substituting the Ser residue at position 16 with Cys or Hcy, substituting Gln residue at position 20 with Cys or Hcy, and linking the two residues with a cross-linker to form a ring. For example, Compound 22 (SEQ ID NO: 23), one of the embodiment examples below, is prepared by substituting $X_{19}$ with Cys, substituting $X_{20}$ with Cys, and linking the two residues with a cross-linker to form a ring.

Also, the above-mentioned acylated oxyntomodulin peptide analog of the present invention may be prepared by taking a naturally-occurring oxyntomodulin and substituting its Ser residue at position 16 with Asp or Glu, substituting the Gln residue at position 20 with Lys or Orn, and forming an intra-molecular lactam ring. For example, Compound 26 (SEQ ID NO: 27), one of the embodiment examples below, is prepared by substituting $X_{19}$ with Asp, $X_{20}$ with Lys, and forming an intramolecular lactam ring; and Compound 14 (SEQ ID NO:15), Compound 19 (SEQ ID NO:20), Compound 20 (SEQ ID NO:21), Compound 24 (SEQ ID NO:25), and Compound 25 (SEQ ID NO:26) are prepared by substituting $X_{19}$ with Glu, $X_{20}$ with Lys, and forming an intramolecular lactam ring.

Also, the above-mentioned acylated oxyntomodulin peptide analog of the present invention may be prepared by taking a naturally-occurring oxyntomodulin and substituting its Ser residue at position 16 with Asp or Glu, substituting Gln residue at position 20 with Lys or Orn, and linking the two residues with a cross-linker to form a ring. For example, Compound 37 (SEQ ID NO:38) and Compound 38 (SEQ ID NO:39) are prepared by substituting $X_{19}$ with Asp, $X_{20}$ with Lys, and linking the two residues with a cross-linker to form a ring; and Compound 33 (SEQ ID NO:34), Compound 34 (SEQ ID NO:35), Compound 35 (SEQ ID NO:36), and Compound 36 (SEQ ID NO:37) are formed by substituting $X_{19}$ with Glu, $X_{20}$ with Lys and linking the two residues with a cross-linker to form a ring.

Also, the above-mentioned acylated oxyntomodulin peptide analog of the present invention may be formed by taking a naturally-occurring oxyntomodulin and substituting its Ser residue at position 16 with Lys or Orn, Gln residue at position 20 with Asp or Glu, and forming an intra-molecular lactam ring. For example, Compound 21 (SEQ ID NO: 22), one of the embodiment examples below, is prepared by substituting $X_{19}$ with Lys, $X_{20}$ with Glu, and forming an intra-molecular lactam ring; and Compound 27 (SEQ ID NO:28) is prepared by substituting $X_{19}$ with Lys, $X_{20}$ with Asp, and forming an intramolecular lactam ring.

Also, the above-mentioned acylated oxyntomodulin peptide analog may be prepared by taking a naturally-occurring oxyntomodulin and substituting its Ser residue at position 16 with Lys or Orn, Gln-20 with Asp or Glu, and linking the two residues with a cross-linker to form a ring. For example, Compound 32 (SEQ ID NO:33), one of the embodiment examples below, is prepared by substituting $X_{19}$ with Lys, $X_{20}$ with Glu, and linking the two residues with a cross-linker to form a ring.

Also, the above-mentioned acylated oxyntomodulin peptide analog may be prepared by taking a naturally-occurring oxyntomodulin and substituting its Ser residue at position 16 with Asp or Glu, Gln-20 with Asp or Glu, and linking the two residues with a cross-linker to form a ring. For example, Compound 23 (SEQ ID NO:24), Compound 29 (SEQ ID NO:30), and Compound 30 (SEQ ID NO:31), a few of the embodiment examples below, are prepared by substituting $X_{19}$ with Glu, $X_{20}$ with Glu and linking the two residues with a cross-linker.

Also, the above-mentioned acylated oxyntomodulin peptide analog may be prepared by taking a naturally-occurring oxyntomodulin and substituting its Ser residue at position 16 with Lys or Orn, Gln residue at position 20 with Lys or Orn, and linking the two residues with a cross-linker to form a ring. For example, Compound 31 (SEQ ID NO:32), one of the embodiment examples below, is prepared by substituting $X_{19}$ with Lys, $X_{29}$ with Lys and linking the two residues with a cross-linker to form a ring.

It is believed that such intramolecular cross-linking stabilizes the alpha helix structure of the peptide, increasing its selectivity for GLP-1 receptor and/or glucagon receptor or increasing pharmacological efficacy (ACS Chem Biol. 2016; 11:324-328).

The oxyntomodulin peptide analog of the present invention may be chemically modified. In particular, each amino acid residue constituting the peptide may be directly connected to various spacers or linkers. Also, each residue may undergo a chemical reaction such as alkylation, disulfide bond formation, metal complexation, amidation, esterification, oxidation, and reduction to be modified to the respective chemical product.

In particular, any carboxy-terminus or amino-terminus present in the structure of the oxyntomodulin peptide analog may undergo reactions such as esterification, amidation, and acylation to yield an analog. Moreover, oxyntomodulin peptide analog of the present invention may be provided as an acid addition salt of any amine group in its structure or a carboxylate salt of any carboxyl group in its structure, or alkali addition salt thereof.

Also, the present invention relates to a pharmaceutical composition comprising the above-mentioned peptide analog as active ingredient and comprising pharmaceutically acceptable excipient for the prevention and treatment of obesity or overweight and diabetes accompanying said conditions.

The term "prevention" in the present invention refers to any and all actions to inhibit or delay the development of the target condition or disease. The term "treatment" in the present invention refers to any and all actions to mitigate, improve, or alleviate the symptoms of a condition or disease that has developed.

In particular, as the peptide analog of the present invention is a dual agonist of both glucagon receptors and GLP-1 receptors, it shows both GLP-1's effects on food intake and glucagon's effects on fat metabolism and energy spending. Therefore, the pharmaceutical composition for the treatment of obesity or overweight and diabetes accompanying said conditions comprising the peptide analog of the present invention may induce medically beneficial effects on weight management by the combination of its excessive fat removal and food intake inhibition effects.

Also, the peptide analog of the present invention and the pharmaceutical composition comprising said peptide analog may be used to prevent or treat diabetes accompanying obesity by lowering blood glucose. In particular, it may be used to treat non-insulin-dependent diabetes accompanying obesity, or type II diabetes. While no limitation of the scope of interpretation to a particular theory is intended, the pharmaceutical composition comprising the peptide analog of the present invention is highly active on GLP-1 receptors which lowers blood glucose, and thus ultimately useful for glycemic control.

Therefore, the pharmaceutical composition comprising the peptide analog of the present invention may be administered alone or in combination with other related pharmaceuticals for direct or indirect treatment of any condition caused by or characterized by overweight, such as treatment and prevention of obesity, morbid obesity, pre-operative morbid obesity, obesity-related inflammation, obesity-related gallbladder disease, obesity-induced sleep apnea, and obesity-accompanying diabetes. Also, the pharmaceutical composition comprising the peptide analog of the present invention may be administered alone or in combination with other related pharmaceuticals to prevent conditions that may result from the effect of weight or may be related to such an effect, such as metabolic syndrome, hypertension, atherosclerosis-induced dyslipidemia, atherosclerosis, arteriosclerosis, coronary heart disease, or stroke.

"Administration" in the present invention refers to introduction of a substance for treatment to a patient with a suitable method. The pharmaceutical composition comprising the peptide analog of the present invention may be administered via various routes and in various forms that enable delivery of the drug to the target tissue and the achieve intended efficacy thereof, including but not limited to, intraperitoneal administration, intravenous administration, intramuscular administration, subcutaneous administration, Intradermal administration, oral administration, topical administration, intranasal administration, intrapulmonary administration, and intrarectal administration.

The pharmaceutical composition comprising the oxyntomodulin peptide analog of the present invention may comprise various pharmaceutically acceptable excipients, including: binders, lubricants, disintegrants, excipients, solubilizers, dispersants, stabilizers, suspending agents, colorants, flavorings, and the like in the case of oral administration; a combination of buffers, preservatives, analgesics, solubilizers, isotonic agents, stabilizers, and the like in the case of injection; and bases, excipients, lubricants, preservatives, and the like in the case of topical administration.

Examples of carriers, excipients, and diluents that may be used in the formulation of the oxyntomodulin peptide analog of the present invention include: lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate or mineral oil.

The pharmaceutical composition comprising the oxyntomodulin peptide of the present invention may be prepared in various ways by combining with the carriers described above. For example, it may be prepared in the form of tablets, troches, capsules, elixirs, suspensions, syrups, wafers, and the like for oral administration; unit dose ampoules or multi-dose forms for injection; and solutions, tablets, pills, capsules, and sustained-release preparations.

The dosage range according to the present invention varies depending on factors such as the patient's weight, age, sex, health, diet, excretion rate, and severity of the condition. For an adult patient, appropriate dosage may be between 0.001 to 500 mg/kg per day.

Advantageous Effects of Invention

The present invention provides a novel acylated oxyntomodulin peptide analog; the peptide analog of the present invention is superior to natural oxyntomodulin in activity on both GLP-1 receptors and glucagon receptors. Particularly, the present invention shows higher biological activity as a glucagon receptor agonist than as a GLP-1 receptors agonist.

Accordingly, the pharmaceutical composition comprising the novel acylated oxyntomodulin peptide analog of the present invention may be usefully applied in the prevention or treatment of conditions caused or characterized primarily by obesity or overweight. Furthermore, it may also be used for the purpose of preventing or treating non-insulin-dependent obesity accompanying obesity or overweight.

BRIEF DESCRIPTION OF DRAWINGS

FIG. 1 is a graph showing the results of body weight loss efficacy evaluation in mice by single injection of acylated oxyntomodulin analog according to the present invention.

FIGS. 2a and 2b are graphs showing the results of body weight loss efficacy evaluation in mice by repeated injection of acylated oxyntomodulin peptide analog according to the present invention for one week;

FIG. 2a shows the body weight loss results;

FIG. 2b shows the cumulative food intake results.

FIGS. 3a and 3b are graphs showing the results of body weight loss efficacy evaluation in rats by repeated injection of acylated oxyntomodulin peptide analog according to the present invention for 5 days;

FIG. 3a shows body weight loss results;

FIG. 3b shows cumulative food intake results.

FIGS. 4a and 4b are graphs showing the body weight loss efficacy evaluation results in mice by repeated injection of acylated oxyntomodulin peptide analog according to the present invention for 10 days;

FIG. 4a shows body weight loss results;

FIG. 4b shows cumulative food intake results.

FIGS. 5a and 5b are graphs showing the body weight loss efficacy results in mice by repeated injection of acylated oxyntomodulin peptide analogs according to the present invention for 10 days;

FIG. 5a shows body weight loss results;

FIG. 5b shows cumulative food intake results.

FIGS. 6a and 6b are graphs showing the body weight loss efficacy evaluation results in mice by repeated injection of the acylated oxyntomodulin peptide analogs according to the present invention for 1 week;

FIG. 6a shows body weight loss results;

FIG. 6b shows cumulative food intake results.

FIGS. 7a, 7b, 7c and 7d are graphs showing the body weight loss efficacy results in mice by repeated injection of acylated oxyntomodulin peptide analogs according to the present invention for 2 weeks;

FIGS. 7a and 7c show body weight loss results;

FIG. 7b shows cumulative food intake results the acylated oxyntomodulin peptide analogs indicated in 7a;

FIG. 7d shows cumulative food intake results of the acylated oxyntomodulin peptide analogs indicated in 7c.

FIGS. 8a and 8b are graphs showing the body weight loss efficacy results in mice by repeated injection of acylated oxyntomodulin peptide analogs according to the present invention for 2 weeks;

FIG. 8a shows body weight loss results;

FIG. 8b shows cumulative food intake results.

FIGS. 9a and 9b are graphs showing the body weight loss efficacy evaluation results in mice by repeated injection of acylated oxyntomodulin peptide analog according to the present invention for 5 days;

FIG. 9a shows body weight loss results;

FIG. 9b shows cumulative food intake results.

FIGS. 10a, 10 and 10c are graphs showing the body weight loss efficacy evaluation results in mice by repeated injection of acylated oxyntomodulin peptide analogs according to the present invention for 4 weeks;

FIG. 10a shows body weight loss results;

FIG. 10b shows body fat mass loss results;

FIG. 10c shows cumulative food intake results.

FIG. 11 is a graph showing the oral glucose tolerance test results in mice of acylated oxyntomodulin peptide analogs according to the present invention.

FIGS. 12a and 12b are graphs showing the results of glycemic control efficacy in mice by repeated injection of acylated oxyntomodulin peptide analog according to the present invention for 6 weeks;

FIG. 12a shows non-fasting blood glucose results;

FIG. 12b shows glycated hemoglobin elevation inhibition results.

FIGS. 13a and 13b are graphs showing the results of glycemic control efficacy in mice by repeated injection of acylated oxyntomodulin peptide analogs according to the present invention for 4 weeks;

FIG. 13a shows non-fasting blood glucose levels over time;

FIG. 13b shows glycated hemoglobin elevation inhibition and improvement.

BEST MODE FOR CARRYING OUT THE INVENTION

The present invention is further described in detail by reference to the following examples and experimental examples. These examples are provided for purposes of illustration only, to help a person skilled in the art understand the invention, and should not in any way be construed as limiting the scope of the present invention.

<Example 1> Synthesis of Acylated Oxyntomodulin Peptide Analog

Peptides comprising part of the amino acids of the present invention or catalog peptide sequences may be synthesized or purchased from commercial peptide synthesis companies, such as American Peptide Company, Bachem, and Anygen.

In the present invention, an auto-synthesizer model Symphony X (synthesis scale: 0.1 mmol) by Protein Technologies Inc was used to synthesize the acylated oxyntomodulin peptide analogs. The structures of Compound 1 (SEQ ID NO: 2) and Compound 38 (SEQ ID NO: 39), which hare acylated oxyntomodulin peptide analogs synthesized according to the present invention, are shown in Table 1 and Table 2. The detailed synthesis procedures are provided below:

A mixture of Fmoc-AA-OH (1 mmol), HBTU (1 mmol), NMM (n-methylmorpholine)(2 mmol) and DMF(7 ml) is added to a resin from which Fmoc has been removed and stirred at room temperature for 1 hour. Drain the reaction solution and wash twice with 7 ml of DMF(N,N-dimethylmethanamide). Fmoc cleavage reaction is performed twice for 5 minutes at room temperature and washed 6 times with DMF (7 ml). This process is repeated using an autosynthesizer to couple the amino acids.

For K(Lys) side synthesis, Fmoc-K(Dde)-OH is used for coupling. For the last H(His), Boc-His(Trt)-OH is used for coupling. Use 2% hydralazine to remove the protected Dde and then couple PEG2, rE, C18, C18 diacid, etc. For lactam ring synthesis, amino acids incorporated into Glu(Oall) and Lys(Alloc) are used for coupling. After protecting group is removed, excess HBTU and DIPEA are used to perform lactam binding. The di-sulfide ring is coupled using Ser amino acid incorporated into the protecting group. After the protecting group is removed, di-sulfide bonding is performed. Coupling is carried out using suitable protecting group-incorporated amino acids at the position to which the cross-linker is to be introduced. After the protecting group is removed, bonding between the cross-linker and the two amino acids is performed using amide coupling reagent.

To 0.1 mmol of the peptide-resin obtained above, add 8 ml of Reagent K (trifluoroacetic acid, water, thioanisole, 1,2-ethandithiol (87.5, 5.0, 5.0, 2.5)) solution after cooling it to 5-10° C. Then, stir at room temperature for 2-3 hours. After draining, wash the resin with a small amount of TFA. Then, the filtrates are combined and added to 100 ml of diethyl ether to crystallized. The resulting solid is filtered to obtain crude peptide. The crude peptide obtained is purified by preparative HPLC to give the desired compound.

Shimadzu AXIMA Assurance MALDI-TOF was used for molecular mass analysis; α-Cyano-4-hydroxycinnamic acid (CHCA) was used as a matrix.

TABLE 1

<STRUCTURES OF ACYLATED OXYNTOMODULIN PEPTIDE ANALOGS>

| Compound | Structure |
|---|---|
| Compound 1 | H-H-S-Q-G-T-F-T-S-D-[Lys(γE-PEG2-PEG2-C18 diacid)]-S-K-Y-L-D-S-R-A-Q-D-F-V-Q-W-L-M-N-T-K-OH |
| Compound 2 | H-H-Aib-Q-G-T-F-T-S-D-[Lys(γE-PEG2-PEG2-C18 diacid)]-S-K-Y-L-D-S-R-A-Q-D-F-V-Q-W-L-M-N-T-K-OH |
| Compound 3 | H-H-Aib-Q-G-T-F-T-S-D-[Lys(γE-PEG2-PEG2-C18 diacid)]-S-K-Y-L-D-Aib-R-A-Q-D-F-V-Q-W-L-M-N-T-K-OH |

TABLE 1-continued

<STRUCTURES OF ACYLATED OXYNTOMODULIN PEPTIDE ANALOGS>

| Compound | Structure |
|---|---|
| Compound 4 | H—H-S-Q-G-T-F-T-S-D—[Lys(γGlu-C18 diacid-PEG2-PEG2-glycolyl)]—S-K-Y-L-D-S-R-R-A-Q-D-F-V-Q-W-L-M-N-T-K-NH$_2$ |
| Compound 5 | H—H-S-Q-G-T-F-T-S-D—[Lys(γGlu-C18 diacid-PEG2-PEG2-glycolyl)]—S-K-Y-L-D-S-R-R-A-Q-D-F-V-Q-W-L-M-N-T-K-R-N-R-N-N-I-A-OH |
| Compound 6 | H—H-Aib-Q-G-T-F-T-S-D—[Lys(γGlu-C18 diacid-PEG2-PEG2-glycolyl)]—S-K-Y-L-D-Aib-R-R-A-Q-D-F-V-Q-W-L-M-N-T-K-R-N-R-N-N-I-A-OH |
| Compound 7 | H—H-Aib-Q-G-T-F-T-S-D—[Lys(γGlu-C18 diacid-PEG2-PEG2-glycolyl)]—S-K-Y-L-D-Aib-R-R-A-Q-D-F-V-Q-W-L-M-N-T-K-R-N-R-N-N-I-A-OH |

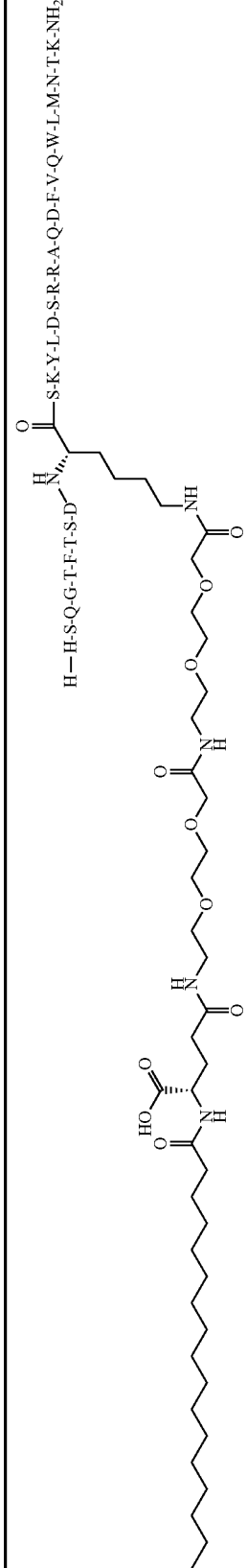
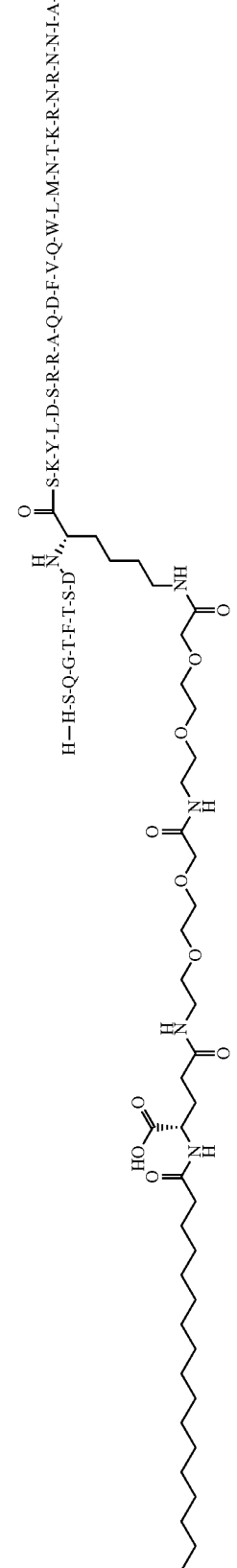
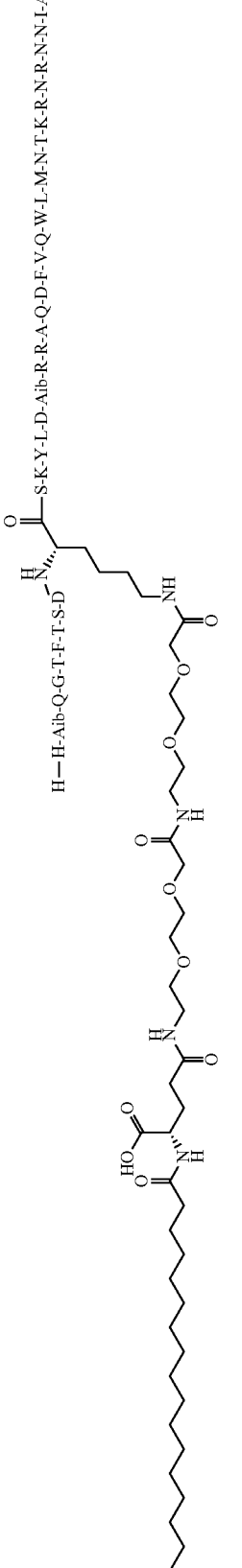
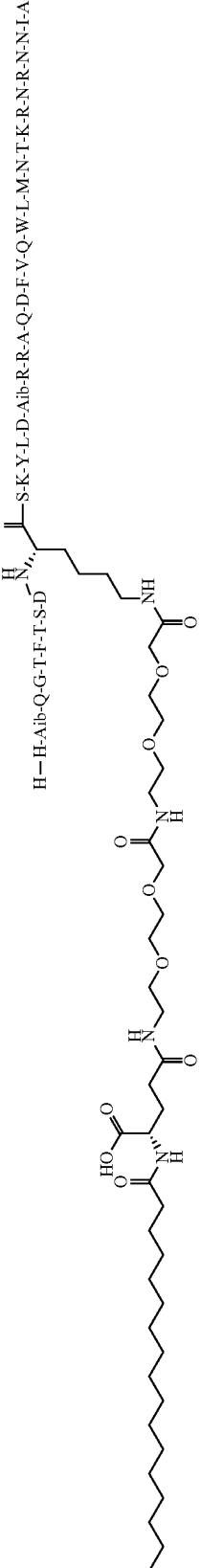

TABLE 1-continued

<STRUCTURES OF ACYLATED OXYNTOMODULIN PEPTIDE ANALOGS>

| Compound | Structure |
|---|---|
| Compound 8 | H—H-Aib-Q-G-T-F-T-S-D—[...]—S-K-Y-L-D-Aib-R-R-A-Q-D-F-V-Q-W-L-M-N-T-K-OH |
| Compound 9 | H—H-Aib-Q-G-T-F-T-S-D—[...]—S-K-Y-L-D-Aib-R-R-A-Q-D-F-V-Q-W-L-M-N-T-K-OH |
| Compound 10 | H—H-Aib-Q-G-T-F-T-S-D—[...]—S-K-Y-L-D-Aib-R-R-A-Q-D-F-V-Q-W-L-M-N-T-K-OH |
| Compound 11 | H—H-Aib-Q-G-T-F-T-S-D—[...]—S-K-Y-L-D-Aib-R-R-A-Q-D-F-V-Q-W-L-M-N-T-K-OH |

TABLE 1-continued
<STRUCTURES OF ACYLATED OXYNTOMODULIN PEPTIDE ANALOGS>
| Compound | Structure |
|---|---|
| Compound 12 | 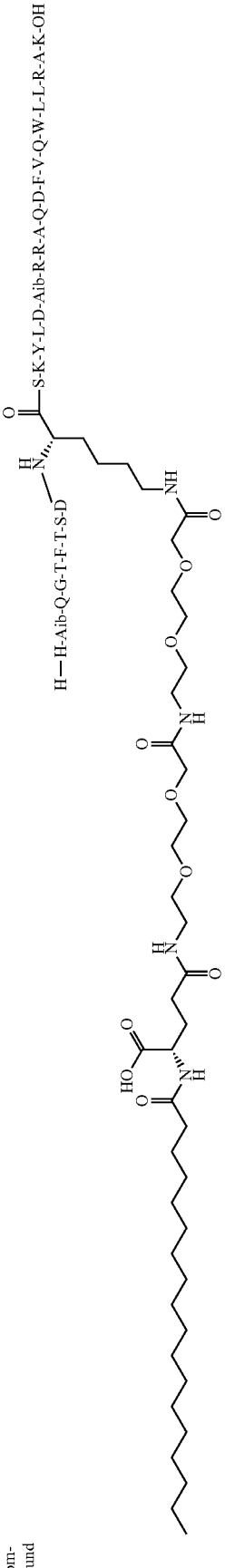 |
| Compound 13 | 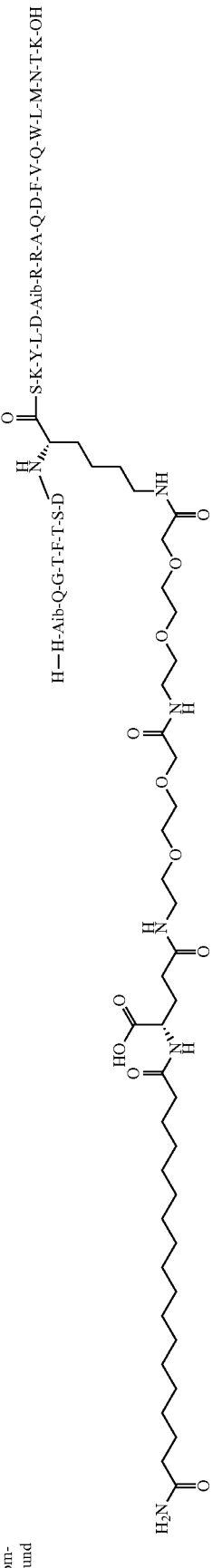 |
| Compound 14 | 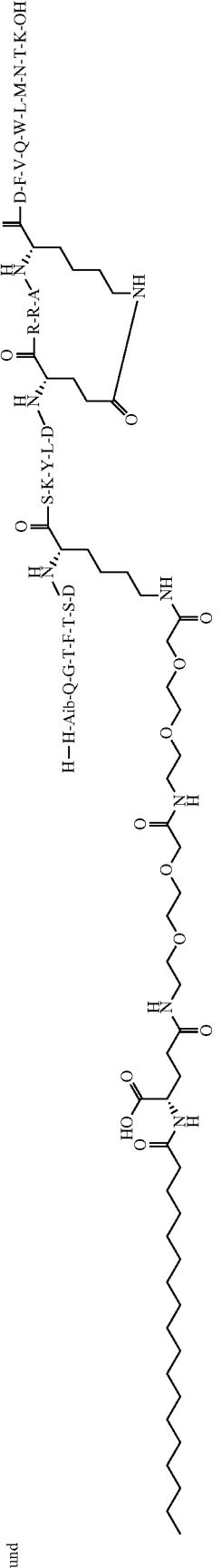 |

TABLE 1-continued

⟨STRUCTURES OF ACYLATED OXYNTOMODULIN PEPTIDE ANALOGS⟩

| Compound | Structure |
|---|---|
| Compound 15 | H—H-Aib-Q-G-T-F-T-S-D-Y-S-K-Y-L-D-[Lys(γGlu-PEG-PEG-Gly-C18 diacid)]-R-R-A-Q-D-F-V-Q-W-L-M-N-T-OH |
| Compound 16 | H—H-Aib-Q-G-T-F-T-S-D-Y-S-K-Y-L-D-Aib-R-A-[Lys(γGlu-PEG-PEG-Gly-C18 diacid)]-D-F-V-Q-W-L-M-N-T-K-OH |
| Compound 17 | H—H-Aib-Q-G-T-F-T-S-D-[Lys(γGlu-PEG-Gly-C18 diacid)]-S-K-Y-L-D-Aib-R-R-A-Q-D-F-V-Q-W-L-M-N-T-K-OH |

TABLE 1-continued

<STRUCTURES OF ACYLATED OXYNTOMODULIN PEPTIDE ANALOGS>

| Compound | Structure |
|---|---|
| Compound 18 | H—H-Aib-Q-G-T-F-T-S-D-[K(γE-C18 diacid-PEG2-PEG2)]-S-K-Y-L-D-Aib-R-R-A-Q-D-F-V-Q-W-L-M-N-T-K-OH |
| Compound 19 | H—H-Aib-Q-G-T-F-T-S-D-[K(PEG2-PEG2-γE-C18 diacid)]-S-K-Y-L-D-[K(γE-R-R-A)]-D-F-V-Q-W-L-M-N-T-K-NH₂ |
| Compound 20 | H—H-Aib-Q-G-T-F-T-S-D-[K(PEG2-PEG2-γE-C18 diacid)]-S-K-Y-L-D-[K(γE-R-R-A)]-D-F-V-Q-W-L-M-N-T-K-OH |
| Compound 21 | H—H-Aib-Q-G-T-F-T-S-D-[K(PEG2-PEG2-γE-C18 diacid)]-S-K-Y-L-D-[K(γE-R-R-A)]-D-F-V-Q-W-L-M-N-T-K-OH |

TABLE 1-continued

<STRUCTURES OF ACYLATED OXYNTOMODULIN PEPTIDE ANALOGS>

| Compound | Structure |
|---|---|
| Compound 22 | H-H-Aib-Q-G-T-F-T-S-D-K(γE-PEG-PEG-C18 diacid)-S-K-Y-L-D-C(-CH2-C6H4-CH2-)-R-R-A-C-D-F-V-Q-W-L-M-N-T-K-OH (bis-thioether xylene bridge) |
| Compound 23 | H-H-Aib-Q-G-T-F-T-S-D-K(γE-PEG-PEG-C18 diacid)-S-K-Y-L-D-[homopiperazine-glutaryl bridge]-R-R-A-[Lys]-D-F-V-Q-W-L-M-N-T-K-OH |
| Compound 24 | H-H-Aib-Q-G-T-F-T-S-D-K(γE-PEG-PEG-PEG-PEG-C18 diacid)-S-K-Y-L-D-[lactam bridge]-R-R-A-[Lys]-D-F-V-Q-W-L-M-N-T-K-NH2 |
| Compound 25 | H-H-Aib-Q-G-T-F-T-S-D-K(γE-PEG-PEG-PEG-PEG-C18 diacid)-S-K-Y-L-D-[lactam bridge]-R-R-A-[Lys]-D-F-V-Q-W-L-M-N-T-K-OH |

TABLE 1-continued

<STRUCTURES OF ACYLATED OXYNTOMODULIN PEPTIDE ANALOGS>

| Compound | Structure |
|---|---|
| Compound 26 | 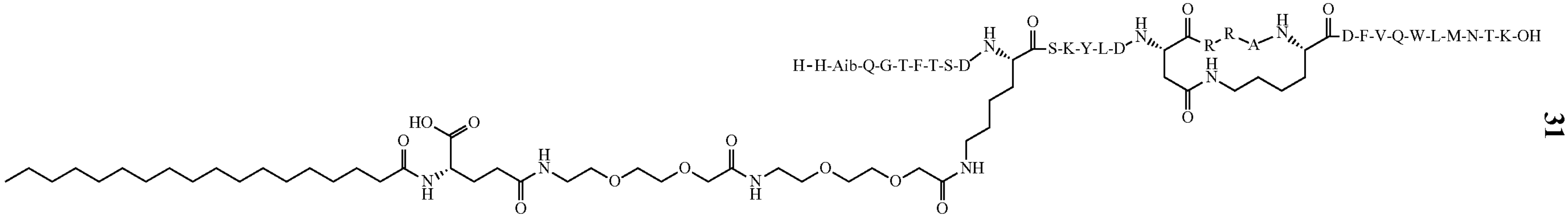 |
| Compound 27 | 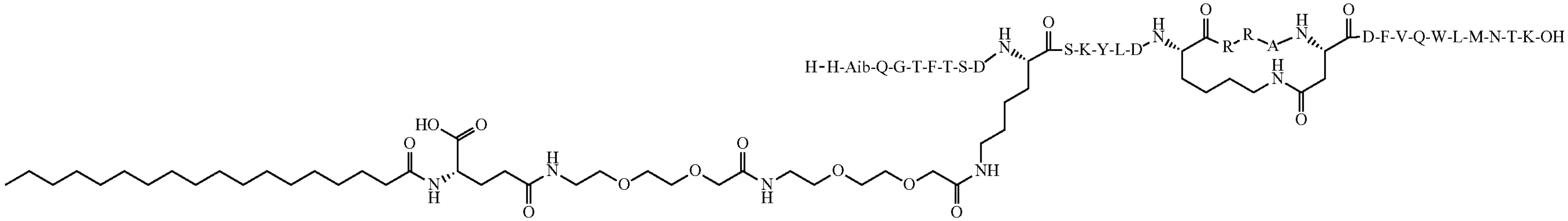 |
| Compound 28 | 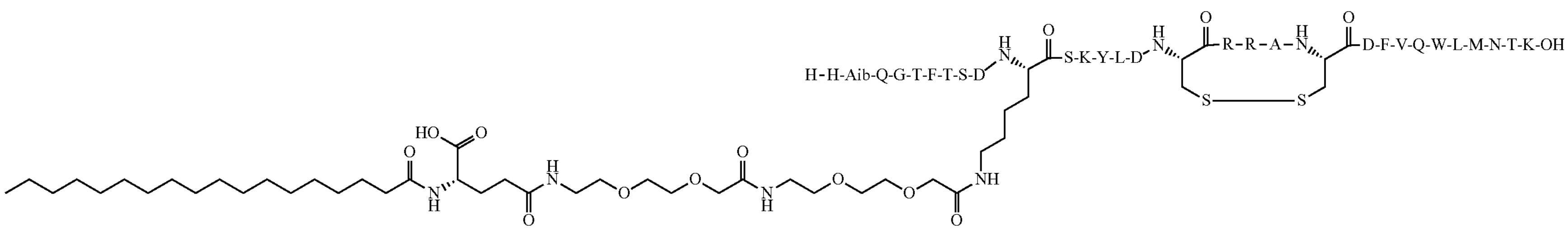 |

TABLE 1-continued

<STRUCTURES OF ACYLATED OXYNTOMODULIN PEPTIDE ANALOGS>

| Compound | Structure |
|---|---|
| Compound 29 | 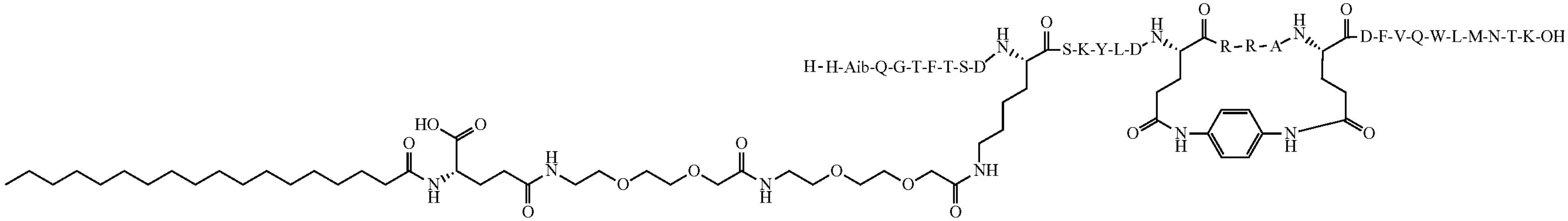 |
| Compound 30 | 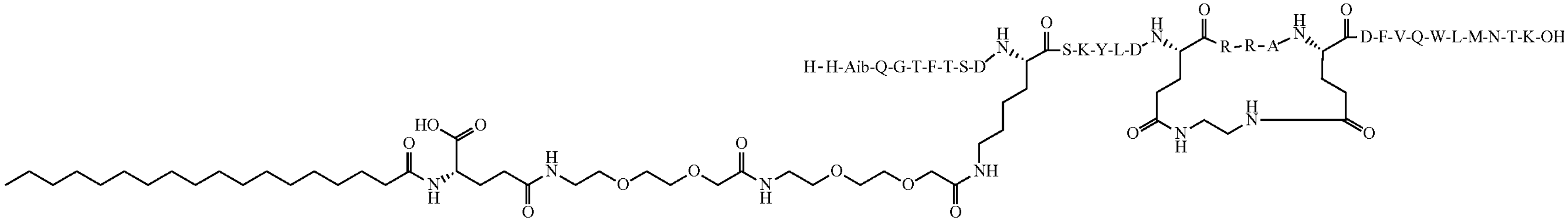 |
| Compound 31 | 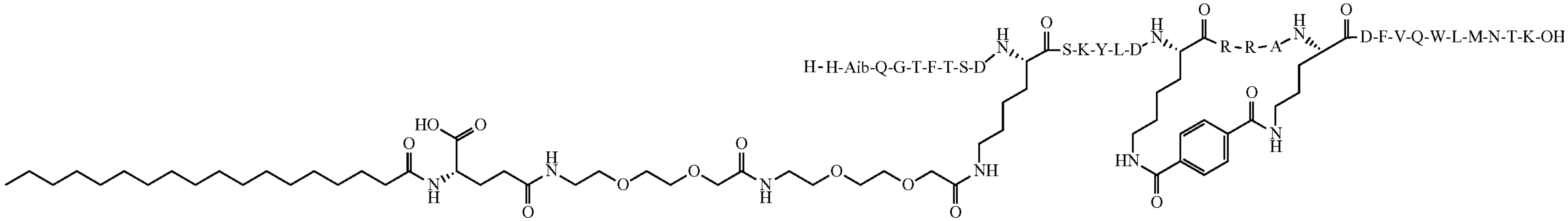 |
| Compound 32 | 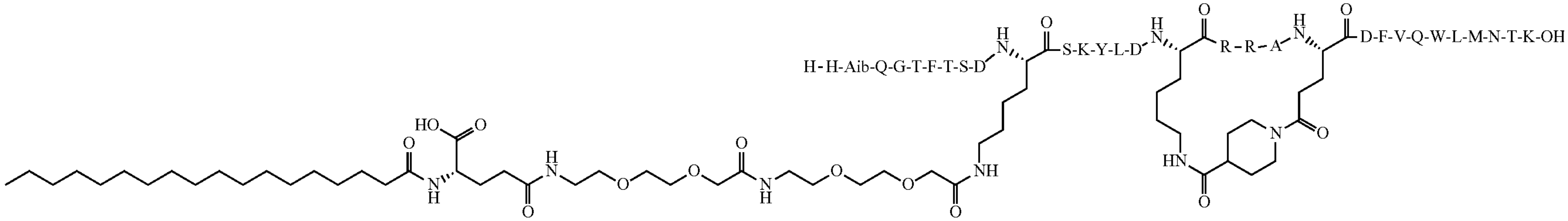 |

TABLE 1-continued

<STRUCTURES OF ACYLATED OXYNTOMODULIN PEPTIDE ANALOGS>

| Compound | Structure |
|---|---|
| Compound 33 | 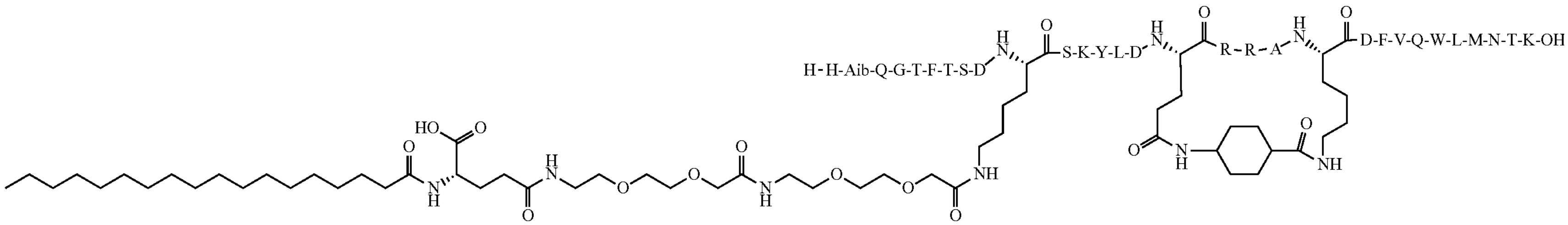 |
| Compound 34 | 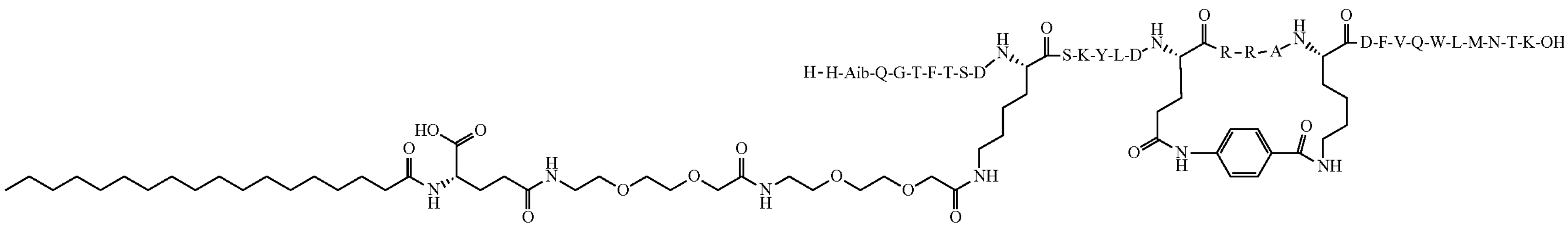 |
| Compound 35 | 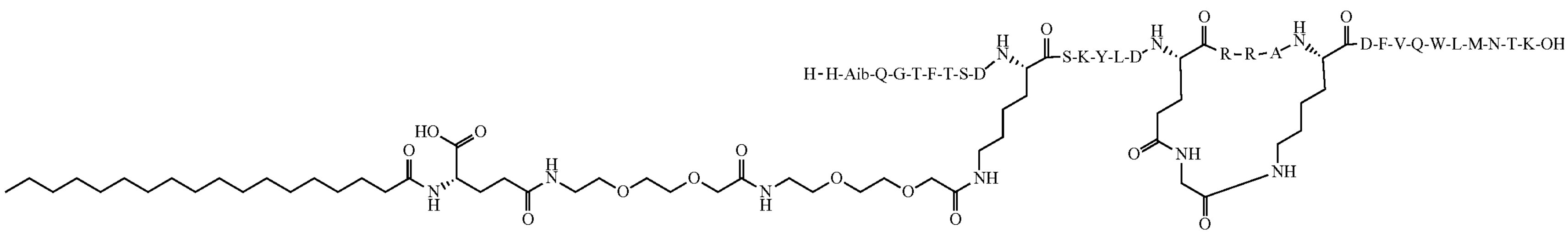 |

TABLE 1-continued

<STRUCTURES OF ACYLATED OXYNTOMODULIN PEPTIDE ANALOGS>

| Compound | Structure |
|---|---|
| Compound 36 | H-H-Aib-Q-G-T-F-T-S-D-S-K-Y-L-D-R-R-A-[K(acylated)]-D-F-V-Q-W-L-M-N-T-K-OH |
| Compound 37 | H-H-Aib-Q-G-T-F-T-S-D-S-K-Y-L-D-R-R-A-[K(acylated)]-D-F-V-Q-W-L-M-N-T-K-OH |
| Compound 38 | H-H-Aib-Q-G-T-F-T-S-D-S-K-Y-L-D-R-R-A-[K(acylated)]-D-F-V-Q-W-L-M-N-T-K-OH |

TABLE 2

<SEQUENCES AND STRUCTURES OF ACYLATED OXYNTOMODULIN PEPTIDE ANALOGS>

| SEQ ID NO. | Name | Sequence |
|---|---|---|
| 1 | OXM (Orig.) | HSQGTFTSDYSKYLDSRRAQDFVQWLMNTKRNRNNIA |
| 2 | Compound 1 | H-HSQGTPTSOZSKYLDSRRAQDFVQWLMNTK-OH |
| 3 | Compound 2 | H-HAibQGTFTSDZSKYLDSRRAQDFVQWLMNTK-OH |
| 4 | Compound 3 | H-HAibQGTFTSDZSKYLDAibRRAQDFVQWLMNTK-OH |
| 5 | Compound 4 | H-HSQGTFTSDZSKYLDSRRAQDFVQWLMNTK-NH$_2$ |
| 6 | Compound 5 | H-HSQGTFTSDZSKYUDSRRAQDFVQWLMNTKRNRNNIA-OH |
| 7 | Compound 6 | H-HAibQGTFTSDZSKYLDAibRRAQDFVQWLMNTK-NH$_2$ |
| 8 | Compound 7 | H-HAibQGTFTSDZSKYLDAibRRAQDFVQWLMNTKRNRNNIA-OH |
| 9 | Compound 8 | H-HAibQGTFTSDZSKYLOAibRRAQDFVQWLMNTK-OH |
| 10 | Compound 9 | H-HAibQGTFTSDZSKYLDAibRRAQPFVQWLMNTK-OH |
| 11 | Compound 10 | H HAibQGTFTSDZSKYLDAibRRAQDFVQWLMNTK-OH |
| 12 | Compound 11 | H-HAibQGTFTSDZSKYLDAibRRAQDFVQWLMNTK-OH |
| 13 | Compound 12 | H-HAibQGTFTSDZSKYLDAibRRAQDFVQWLLRAK-OH |
| 14 | Compound 13 | H-HAibQGTFTSDZSKYLDAibRRAQDFVQWLMNTK-OH |
| 15 | Compound 14 | H-HAibQGTFTSDZSKYLDERRAKDFVQWLMNTK-OH<br>(Lactam ting formed between E and K> |
| 16 | Compound 15 | H-HAibQGTFTSDYSKYLDZRRAQDFVQWLMNTK-OH |
| 17 | Compound 16 | H-HAibQGTFTSDYSKYLDAibRRAZDFVQWLMNTK-OH |
| 18 | Compound 17 | H-HAibQGTFTSDZSKYLDAibRRAQDFVQWLMNTK-OH |
| 19 | Compound 18 | H-HAibQGTFTSDZSKYLDAibRRAQDFVQYVLMNTK-OH |
| 20 | Compound 19 | H-HAibQGTFTSDZSKYLDERRAKDFVQWLMNTK-NH$_2$<br>(Lactam ring formed between E and K) |
| 21 | Compound 20 | H-HAibQGTFTSDZSKYLDERRAKDFVQWLMNTK-OH<br>(Lactam ring formed between E and K) |
| 22 | Compound 21 | H-HAibQGTFTSDZSKYLDKRRAEDFVQWLMNTK-OH<br>(Lactam ring formed between K and E) |
| 23 | Compound 22 | H-HAibQGTFTSDZSKYLDCRRACDFVQWLMNTK-CH<br>(A ring formed between C and C via 1,3-phenyhenedimethyl cross-link) |
| 24 | Compound 23 | H-HAibQGTFTSDZSKYLDERRAEDFVQWLMNTK-OH<br>(A ring formed between E and E via 1,4-piperazinyl cross-link) |
| 25 | Compound 24 | H-HAibQGFTFTSDZSKYLDERRAKDFVQWLMTK-NH2<br>(lactam ring formed between E and K) |
| 26 | Compound 25 | H-HAibQGTFTSDZSKYLDERRAKDFVQWLMNTK-OH<br>(Lactam ring formed between E and K) |
| 27 | Compound 26 | H-HAibQGTFTSDZSKYLDDRRAKDFVQWLMNTK-OH<br>(Lactam ring formed between D and K) |
| 28 | Compound 27 | H-HAibQGTFTSDZSKYLDKRRADDFVQWLMNTK-OH<br>(Lactam ring formed between K and D) |
| 29 | Compound 28 | H-HAibQGTFTSDZSKYLDCRRACDFVQWLMNTK-OH<br>(Di-sulfide ring formed between C and C) |
| 30 | Compound 29 | H-HAibQGTFTSDZSKYLDERRAEDFVQWLMNTK-OH<br>(A ring formed between E and E via 1,4-phenylenediamino cross-link) |

TABLE 2-continued

<SEQUENCES AND STRUCTURES OF ACYLATED OXYNTOMODULIN PEPTIDE ANALOGS>

| SEQ ID NO. | Name | Sequence |
|---|---|---|
| 31 | Compound 30 | H-HAibQGTFTSDZSKYLDERRAEDFVQWLMNTK-OH<br>(A ring formed between E and E via 1,2-ethylenediamino cross-link |
| 32 | Compound 31 | H-HAibQGTFTSDZSKYLDKRRAKDFVQWLMNTK-OH<br>(A ring formed between K and K via 1,4-phenylenebiscarbonyl cross-link) |
| 33 | Compound 32 | H-HAibQGTFTSDZSKYLDKRRAEDFVQWLMNTK-OH<br>(A ring formed between K and E via 4-carbonylpiperidin-1-yl cross-link) |
| 34 | Compound 33 | H-HAibQGTFTSDZSKYLDERRAKDFVQWLMNTK-OH<br>(A ring formed between E and K via 1-aminocyclohexan-4-carbonyl cross-link) |
| 35 | Compound 34 | H-HAibQGTFTSDZSKYLDERRAKDFVQWLMNTK-OH<br>(A ring formed between E and K via 4-aminobenzoyl cross-link) |
| 36 | Compound 35 | H-HAibQGTFTSDZSKYLDERRAKDFVQWLMNTK-OH<br>(A ring formed between E and K via glycine cross-link) |
| 37 | Compound 36 | H-HAibQGTFTSDZSKYLDERRAKDFVQWLMNTK-OH<br>(A ring formed between E and K via leucine cross-link) |
| 38 | Compound 37 | H-HAibQGTFTSDZSKYLDDRRAKDFVQWLMNTK-OH<br>(A ring formed between D and K via glycine cross-link) |
| 39 | Compound 38 | H-HAibQGTFTSDZSKYLDDRRAKDFVQWLMNTK-OH<br>(A ring formed between D and K via leucine cross-link) |

Z is a modified form of Lys: specifically, Lys with side chain bonded to polymer, spacer, or/and lipophilic lipid.
Z takes on the following specific forms depending on the compound:
For Compounds 1-7, 12, 14-16, 19, 21-23, and 26-38: Lys([(2-(2-(2-aminoethoxy)ethoxy)acetoyl)$_2$]-[gamma glutamicacid]-[octadecanoyl])
For Compound 8: Lys([(2-(2-(2-aminoethoxy)ethoxy)acetoyl)$_2$]-[gamma glutamicacid]-[icosanoyl])
For Compound 9: Lys([(2-(2-(2-aminoethoxy)ethoxy)acetoyl)$_2$]-[gamma glutamicacid]$_2$]-[octadecanoyl])
For Compounds 10 and 20: Lys([(2-(2-(2-aminoethoxy)ethoxy)acetoyl)$_3$]-[gamma glutamicacid]-[octadecanoyl])
For Compound 11: Lys([Gly-Gly-Ser-Gly-Ser-Gly]-[gamma glutamic acid]-[octadecanoyl])
For Compound 13: Lys([(2-(2-(2-aminoethoxy)ethoxy)acetoyl)$_2$]-[gamma glutamicacid]-[17-aminocarbonylheptadecanoyl])
For Compound 17: Lys([(2-(2-(2-aminoethoxy)ethoxy)acetoyl)]-[gamma glutamicacid]-[octadecanoyl])
For Compounds 18, 24, and 25: Lys([(2-(2-(2-aminoethoxy)ethoxy)acetoyl)$_4$]-[gamma glutamicacid]-[octadecanoyl])

<Comparative Example 1> Synthesis of Oxyntomodulin Peptide Analog

To compare with the present invention, oxyntomodulin peptide analogs having structural similarities were synthesized by the method of Example 1. Compound 39 below is a non-acylated oxyntomodulin peptide analog. Compounds 40 and 41 are oxyntomodulin peptide analogs acylated at different positions. Compounds 42 and 46 are oxyntomodulin peptide analogs with acylation at different terminal ends. Compound 47, disclosed in Korean Patent Publication No. 2012-139579, is non-acylated oxyntomodulin peptide analog with a ring structure. The structures of synthesized oxyntomodulin peptide analogs of Compounds 39 through 47 above are shown in Table 3 and Table 4.

TABLE 3

<STRUCTURES OF OXYNTOMODULIN PEPTIDE ANALOGS>

| Compound | Structure |
|---|---|
| Compound 39 | H—H-Aib-Q-G-T-F-T-S-D-K-S-K-Y-L-D-Aib-R-R-A-Q-D-F-V-Q-W-L-M-N-T-K-OH |
| Compound 40 | (structure shown) |
| Compound 41 | (structure shown) |
| Compound 42 | (structure shown) |

TABLE 3-continued

<STRUCTURES OF OXYNTOMODULIN PEPTIDE ANALOGS>

| Compound | Structure |
|---|---|
| Compound 43 | H-H-Aib-Q-G-T-F-T-S-D-[linker-C16 diacid]-S-K-Y-L-D-Aib-R-A-Q-D-F-V-Q-W-L-M-N-T-K-OH |
| Compound 44 | H-H-Aib-Q-G-T-F-T-S-D-[linker-C16 diacid]-S-K-Y-L-D-Aib-R-A-Q-D-F-V-Q-W-L-M-N-T-K-OH |
| Compound 45 | H-H-Aib-Q-G-T-F-T-S-D-[linker-C16-Gly]-S-K-Y-L-D-Aib-R-A-Q-D-F-V-Q-W-L-M-N-T-K-OH |
| Compound 46 | H-H-Aib-Q-G-T-F-T-S-D-[linker-C16-Val]-S-K-Y-L-D-Aib-R-A-Q-D-F-V-Q-W-L-M-N-T-K-OH |

TABLE 3-continued

<STRUCTURES OF OXYNTOMODULIN PEPTIDE ANALOGS>

| Compound | Structure |
|---|---|
| Compound 47 | H-H-Aib-Q-G-T-F-T-S-D-Y-S-K-Y-L-D-[cyclic lactam]-K-R-A-[cyclic lactam]-E-F-V-Q-W-L-M-N-T-K-C-OH |

TABLE 4

<SEQUENCES AND STRUCTURES OF OXYNTOMODULIN PEPTIDE ANALOGS>
SEQUENCES AND STRUCTURES OF OXYNTOMODULIN PEPTIDE ANALOGS

| SEQ ID NO. | Name | Sequence |
|---|---|---|
| 40 | Compound 39 | H-HAibQGTFTSDKSKYLDAibRRAQDFVQWLMNTK-OH |
| 41 | Compound 40 | H-HAibQGTFTSZYSKYLDAibRRAQDFVQWLMNTK-OH |
| 42 | Compound 41 | H-HSQGTFTSDYSKYLDSRRAQDFVQWLMNTZ-OH |
| 43 | Compound 42 | H-HAibQGTFTSDZSKYLDAibRRAQDFVQWLMNTK-OH |
| 44 | Compound 43 | H-HAibQGTFTSDZSKYLDAibRRAQDFVQWLMNTK-OH |
| 45 | Compound 44 | H-HAibQGTFTSDZSKYLDAibRRAQDFVQWLMNTK-OH |
| 46 | Compound 45 | H-HAibQGTFTSDZSKYLDAibRRAQDFVQWLMNTK-OH |
| 47 | Compound 46 | H-HAibQGTFrSQZSKYLDAibftRAQDPVQWLMNTK-QH |
| 48 | Compound 47 | H-HAibQGTFTSDYSKYLDEKRAKEFVQWLMNTKC-OH (Lactam ring formed between E and K) |

Z is a modified form of Lys; specifically, Lys with side chain bonded to polymer, spacer, or/and lipophilic lipid.
Z takes on the following specific forms depending on the compound:
For Compounds 40 and 41: Lys([(2-(2-(2-aminoethoxy)ethoxy)acetoyl)₂]-[gammaglutamicacid]-[octadecanoyl])
For Compound 42: Lys([(2-(2-(2-aminoethoxy)ethoxy)acetoyl)₂]-[gammaglutamicacid]-[15-carboxypeptadecanoyl])
For Compound 43: Lys([(2-(2-(2-aminoethoxy)ethoxy)acetoyl)₂]-[gammaglutamicacid]-[17-carboxyheptadecanoyl])
For Compound 44: Lys([(2-(2-(2-aminoethoxy)ethoxy)acetoyl)₂]-[gammaglutamicacid]-[19-carboxypeptadecanoyl])
For Compound 45: Lys([(2-(2-(2-aminoethoxy)ethoxy)acetoyl)₂]-[gammaglutamicacid]-[15-(N-(carbpxymethyl)amino)carbonylnonadecanoyl])
For Compound 46: Lys([(2-(2-(2-aminoethoxy)ethoxy)acetoyl)₂]-[gammaglutamicacid]-[15-(N-(1s)-(1-carboxy-2-methylpropyl)amino(carbonylpentadecanoyl])

<Experimental Example 1> GLP-1 and Glucagon Receptors Activation Assay

Human GLP-1 or glucagon receptors were transiently overexpressed in cells, so that the analog of the present invention could activate the receptors resulting in a rise in cyclic adenosine monophosphate (cAMP), which sequentially activates cyclic adenosine monophosphate response elements (CRE). Then, the resulting increased luciferase activity was evaluated as a measurement of the effect on each receptor activation.

GLP-1 and glucagon were used as positive control in respective evaluation. Liraglutide and Semaglutide, which are GLP-1 agonists approved for treatment of diabetes, and MEDI0382, an oxyntomodulin peptide analog that is in Phase II clinical trial, (Diabetes, Obesity and Metabolism 2016; 18: 1176-1190, Lancet 2018; 391: 2607-2618) as well as Compounds 39 through 47 above were synthesized and used as Comparative Examples.

Human GLP-1 or glucagon expression vector ("OriGene" hereafter) was transiently transfected into Chinese hamster ovary cells (CHO-K1), with plasmid DNAs that can induce expression of firefly luciferase or *Renilla* luciferase (respectively), using Lipofectamine Plus Reagent (Invitrogen). After 3 hours of transfection, medium was exchanged to Alpha Minimal Essential Medium (α-MEM) comprising 10% fetal bovine serum (FBS). Next day, the medium was exchanged to α-MEM comprising the analog of the present invention and 0.1% bovine serum albumin (BSA). After 6 hours, dual luciferase assay reagent was added in the same amount as the medium in which the cells were submerged, and firefly luciferase and *Renilla* luciferase activities were continuously measured. Firefly luciferase activity values were corrected against *Renilla* luciferase activity to yield transfection efficiency.

To measure the efficacy of receptor activity, multi-concentration test was performed on the analog of the present invention to obtain the relative activation (%) of the maximum effect of the analog on either GLP-1 or glucagon, and the concentration indicating 50% activation ($EC_{50}$) was calculated using non-linear regression analysis. The resulting values are shown in Table 5.

TABLE 5

<ACYLATED OXYNTOMODULIN PEPTIDE ANALOGS AND THEIR ABILITY TO ACTIVATE HUMAN GLP-1 AND GLUCAGON RECEPTORS>

| | | $EC_{50}$(pM) | |
|---|---|---|---|
| Structure | Compound | On GLP-1 receptors | On glucagon receptors |
| Control | GLP-1 | A | — |
| | Glucagon | — | A |
| Examples | Compound 1 | A | B |
| | Compound 2 | A | A |
| | Compound 3 | A | A |
| | Compound 4 | A | B |
| | Compound 5 | A | B |
| | Compound 6 | A | A |
| | Compound 7 | A | A |
| | Compound 8 | B | B |
| | Compound 9 | A | A |
| | Compound 10 | A | A |
| | Compound 11 | A | B |
| | Compound 12 | A | A |
| | Compound 13 | B | B |
| | Compound 14 | A | A |
| | Compound 15 | A | A |
| | Compound 16 | A | A |
| | Compound 17 | A | A |
| | Compound 18 | A | A |
| | Compound 19 | A | A |
| | Compound 20 | A | A |

TABLE 5-continued

<ACYLATED OXYNTOMODULIN PEPTIDE ANALOGS
AND THEIR ABILITY TO ACTIVATE
HUMAN GLP-1 AND GLUCAGON RECEPTORS>

| | | $EC_{50}$(pM) | |
|---|---|---|---|
| Structure | Compound | On GLP-1 receptors | On glucagon receptors |
| | Compound 21 | A | A |
| | Compound 22 | A | A |
| | Compound 23 | A | A |
| | Compound 24 | A | B |
| | Compound 25 | A | A |
| | Compound 26 | A | A |
| | Compound 27 | A | A |
| | Compound 28 | C | C |
| | Compound 29 | A | A |
| | Compound 30 | A | A |
| | Compound 31 | A | A |
| | Compound 32 | A | A |
| | Compound 33 | A | A |
| | Compound 34 | A | A |
| | Compound 35 | A | A |
| | Compound 36 | A | A |
| | Compound 37 | A | A |
| | Compound 38 | A | A |
| Comparative | Oxyntomodulin | B | B |
| Examples | Liraglutide | B | — |
| | Semaglutide | B | — |
| | MEDI0382 | A | B |
| | Compound 39 | D | D |
| | Compound 40 | C | D |
| | Compound 41 | C | D |
| | Compound 42 | C | D |
| | Compound 43 | D | D |
| | Compound 44 | C | D |
| | Compound 45 | C | C |
| | Compound 46 | C | C |
| | Compound 47 | A | B |

* A: below 10 pM; B: 10-100 pM; C:100-1000 pM; D: above 1000 pM

Experimental results show that the compounds of acylated oxyntomodulin analogs according to the present invention have significantly lower $EC_{50}$ values for GLP-1 and glucagon receptors than the endogenous oxyntomodulin hormone, indicating superior activity on GLP-1 and glucagon receptors. They also showed superior activity on GLP-1 receptors compared to Liraglutide and Semaglutide, which are current diabetes drugs in the market. They also showed better activity on glucagon receptors and similar activity on GLP-1 receptors compared to MEDI0382, which is an oxyntomodulin peptide analog currently in clinical trial.

Compound 3, an acylated oxyntomodulin peptide analog according to the present invention, showed a much higher activity on GLP-1 and glucagon receptors than comparative example Compound 39, a non-acylated oxyntomodulin peptide analog. As such, acylation of oxyntomodulin peptide analogs is believed to have a significant effect on activity increase.

Also, Compound 40, a comparative example with acylation at $X_2$, and Compound 41, a comparative example acylated at $X_{14}$, showed much lower activity on GLP-1 and glucagon receptors compared to Compounds 3, 15, and 16 according to the present invention with acylation at $X_3$, $X_9$, and $X_{10}$ positions, respectively. This seems to indicate that the position of acylation of oxyntomodulin peptide analogs has a significant effect on their activity.

Compounds 3, 10, 17, and 18, acylated according to the present invention, have 1, 2, 3, and 4 (respectively) 2-(2-(2-aminoethoxy)ethoxy)acetoyl groups as polymeric moiety of $Z_1$. There was no difference in in vitro activity based on the number of 2-(2-(2-aminoethoxy)ethoxy)acetoyl groups. All showed outstanding activity on GLP-1 and glucagon receptors.

Compounds 42, 43, and 44 are acylated comparative examples having carboxylic acid at the terminal of lipophilic lipid moiety as $Z_2$. They showed lower activity on GLP-1 and glucagon receptors regardless of lipid carbon length compared to the acylated compounds according to the present invention such as Compound 3 whose lipophilic lipid moiety terminal is hydrocarbon. Comparative example Compounds 45 and 46 having lipophilic lipid moiety terminal bonded to carboxylic acid and Gly and Val as $Z_2$ showed lower activity on GLP-1 and glucagon receptors compared to Compound 3 and others according to the present invention whose lipophilic lipid moiety terminal is hydrocarbon, indicating that acylated compounds with polar substituents at lipophilic lipid moiety terminal as $Z_2$ have low in vitro activity.

Comparative example Compound 47, a non-acylated oxyntomodulin cyclic peptide analog, showed lower activity on glucagon receptors compared to Compound 14 according to the present invention having the same type of intramolecular lactam ring structure. It can be inferred that acylation of oxyntomodulin peptide analogs leads to increased activity.

Compound 28, which is an acylated oxyntomodulin cyclic peptide analog according to the present invention, has an intramolecular disulfide bond. It showed lower activity on GLP-1 and glucagon receptors compared to Compound 22, another acylated oxyntomodulin cyclic peptide analog. It can be inferred that the size of the intramolecular ring of an acylated oxyntomodulin cyclic peptide analog affects its activity.

<Experimental Examples 2> Body Weight Loss Efficacy Evaluation by Single Injection of Peptides According to the Present Invention To evaluate body weight loss efficacy of the acylated oxyntomodulin peptide analog according to the present invention, male laboratory mice (C57BL/6 mouse) were provided with diet containing high fat. Mice induced to obesity by the high fat diet were assigned to groups by body weight before the experiment began. Compound 3 of the present invention was prepared in distilled water containing 0.01% Tween80 to a dosage of 100 nmol/kg. This was injected once subcutaneously into the mouse. Afterward, body weight and food intake was measured once a day, at the same time each day. The results are shown in FIG. 1.

Although there was no significant difference in cumulative food intake against the control group injected with vehicle only, body weight loss was seen in the group injected with Compound 3 against the control group; the effect lasted for 4 days. This indicates that the oxyntomodulin peptide analog of the present invention can have a body weight loss effect maintained for a period of time with a single administration thanks to the improved chemical stability, compared to oxyntomodulin, which requires at least 1 administration per day to be effective due to its in vivo instability and very short half-life.

<Experimental Example 3> Body Weight Loss Efficacy Evaluation by 1-Week Repeated Injection of the Peptide of the Present Invention This experiment aimed to compare the body weight loss efficacy of the acylated oxyntomodulin peptide analog according to the present invention with commercially available diabetes/obesity treatments. Male laboratory mice (C57BL/6 mouse) were provided with diet containing high fat. The mice with high-fat-diet-induced obesity were separated into groups by body weight before the experiment began. Compound 3, an example according to the present invention, was prepared in distilled water containing 0.01% Tween80 to a dosage of 100 nmol/kg or 300 nmol/kg. As control, Liraglutide, commercially available diabetes/obesity treatment, was prepared in the same vehicle to a dosage of 100 nmol/kg. Afterwards, both were injected subcutaneously for 6 days, once per day, as indicated in Table 6. Body weight and food intake was measured once a day, at the same time each day, to compare body weight loss efficacy of the acylated oxyntomodulin analog against Liraglutide. On day 7, administration was stopped and body weight recovery was checked. The results are shown in FIGS. 2a and 2b.

TABLE 6

| Group | Drug and dose administered | Method of administration | |
|---|---|---|---|
| Comparison group | Liraglutide, 100 nmol/kg/QD | S.C | once a day × 6 |
| Experimental groups | Compound 3, 100 nmol/kg/QD Compound 3, 300 nmol/kg/QD | | |

There was no significant difference in cumulative food intake between Compound 3 and Liraglutide groups injected with identical dosage of 100 nmol/kg. Nonetheless, Liraglutide showed body weight loss of approximately 12.2%, whereas Compound 3 showed body weight loss of approximately 24.6%. Also, injecting Compound 3 at 300 nmol/kg showed approximately 37.8% of body weight loss. The acylated oxyntomodulin peptide analog of the present invention showed more than double the dose-dependent body weight loss effect against Liraglutide and maintained lower body weight against vehicle control group even after discontinuation.

<Experimental Example 4> Body Weight Loss Efficacy Evaluation by 5-Day Repeated Injection of Peptide According to the Present Invention This experiment aimed to find the maximum body weight loss effect of the acylated oxyntomodulin peptide analog of the present invention. Male laboratory rats (Wistar rat) were provided with diet containing high fat. The rats with high-fat-diet-induced obesity were separated by body weight into groups before the experiment began. Compound 3 of the present invention was prepared in distilled water containing 0.01% Tween80 to a dose of 100 nmol/kg or 300 nmol/kg, which was injected subcutaneously once a day for a total of 4 days as indicated in Table 7. Body weight and food intake was measured once per day at the same time each day to measure the body weight loss efficacy over time compared to the initial body weight. On day 5, administration was stopped and body weight recovery was checked. The results are shown in FIGS. 3a and 3b.

TABLE 7

| Group | Drug and dose administered | Method of administration | |
|---|---|---|---|
| Experimental groups | Compound 3, 100 nmol/kg/QD Compound 3, 300 nmol/kg/QD | S.C | once a day × 4 |

The group injected with Compound 3 showed significant difference in cumulative food intake against vehicle control group. Both dosages showed a body weight loss efficacy of approximately 12.5%. Lower body weight against vehicle control was maintained even after discontinuation.

<Experimental Example 5> Body Weight Loss Efficacy Evaluation by 10-Day Repeated Injection of Peptide of the Present Invention This experiment aimed to compare the body weight loss efficacy of acylated oxyntomodulin peptide analog according to the present invention against commercially available diabetes treatments. Male laboratory mice (C57BL/6 mouse) were given diet containing high fat. The mice with high-fat-diet-induced obesity were separated into groups by body weight before the experiment began. Compound 3 of the present invention was prepared in distilled water containing 0.01% Tween80 to a dose of 100 nmol/kg or 300 nmol/kg. Semaglutide, a commercially available diabetes treatment, was prepared in the same vehicle to a dose of 100 nmol/kg. Then, they were subcutaneously injected once every 3 days for a total of 10 days as indicated in Table 8. Body weight and food intake was measured once per day at the same time each day to compare the body weight loss efficacy of the acylated oxyntomodulin peptide analog against Semaglutide. The results are shown in FIGS. 4a and 4b.

TABLE 8

| Group | Drug and dose administered | Method of administration | |
|---|---|---|---|
| Comparison | Semaglutide, 100 nmol/kg/Q3D | S.C | once every 3 days × 4 |
| Experimental | Compound 3, 100 nmol/kg/Q3D Compound 3, 300 nmol/kg/Q3D | | |

Compound 3 showed higher cumulative food intake against Semaglutide at the same dosage (100 nmol/kg) but still showed superior body weight loss efficacy against Semaglutide (Compound 3: 13.9%, Semaglutide: 9.7%). Also, Compound 3 at 300 nmol/kg showed body weight loss of approximately 16.9%. The acylated oxyntomodulin peptide analog according to the present invention showed superior dose-dependent body weight loss efficacy against Semaglutide.

<Experimental Example 6> Body Weight Loss Efficacy Evaluation by 10-Day Repeated Injection of Peptide According to Present Invention This experiment aimed to compare the body weight loss efficacy of acylated oxyntomodulin peptide analogs according to the present invention with varying structures—the number of polymers and presence of cyclic peptide formation. Male laboratory mice (C57BL/6 mouse) were given diet containing high fat. The mice with high-fat-diet-induced obesity were separated into groups by body weight before the experiment began. Compounds 3, 10, and 14 were prepared in distilled water containing 0.01% Tween80 to a dose of 100 nmol/kg, and then injected subcutaneously once every 3 days for a total of 10 days as indicated in Table 9. Body weight and food intake was measured once per day at the same time each day to compare Compound 3 against Compounds 10 and 14 on body weight loss efficacy. The results are shown in FIGS. 5a and 5b.

TABLE 9

| Group | Drug and dose administered | Method of administration | |
|---|---|---|---|
| Experimental | Compound 3, 100 nmol/kg/Q3D<br>Compound 10, 100 nmol/kg/Q3D<br>Compound 14, 100 nmol/kg/Q3D | S.C | once every 3<br>days × 4 |

At same dosage, Compounds 10 and 14 showed cumulative food intake reduced by 20% and 27% respectively against vehicle control group. Cumulative food intake on Compound 3 decreased by approximately 17%. All three compounds showed outstanding body weight loss efficacy of approximately 19-22% from initial body weight. The cyclic peptide Compound 14 had slightly better results than Compounds 3 and 10.

<Experimental Example 7> Body Weight Loss Efficacy Evaluation by 1-Week Repeated Injection of Peptide of Present Invention This experiment aimed to compare the body weight loss efficacy of acylated oxyntomodulin peptide analogs of varying structures—the number of lipophilic lipid moiety or polymers within the peptide. Male laboratory mice (C57BL/6 mouse) were given diet containing high fat. The mice with high-fat-diet-induced obesity were separated into groups by body weight before the experiment began.

Compounds 3, 13 and 18 according to the present invention were prepared in distilled water containing 0.01% Tween80 to a dosage of 100 nmol/kg and as indicated in Table 10 injected subcutaneously once every 3 days for a total of 7 days. Body weight and food intake was measured once per day at the same time each day. Body weight loss efficacy of Compound 3 was compared against Compounds 13 and 18. The results are shown in FIGS. 6a and 6b.

TABLE 10

| Group | Drug and dose administered | Method of administration | |
|---|---|---|---|
| Experimental | Compound 3, 100 nmol/kg/Q3D<br>Compound 13, 100 nmol/kg/Q3D<br>Compound 18, 100 nmol/kg/Q3D | S.C | once every 3<br>days × 3 |

At same dosage, Compound 18 showed similarly outstanding body weight loss efficacy to Compound 3, whereas Compound 13 did not have any significant effect on body weight. Compound 13 showed about 10 times less in vitro efficacy than Compound 3 and was consistent in animal testing, confirming the loss of body weight loss efficacy as a result of the terminal structure of lipophilic lipid moiety, confirming structural importance.

<Experimental Example 8> Body Weight Loss Efficacy Evaluation by 2-Week Repeated Injection of Peptide According to Present Invention This experiment aimed to compare the body weight loss efficacy of acylated oxyntomodulin peptide analogs according to the present invention with varying cyclic peptide structures. Male laboratory mice (C57BL/6 mouse) were given diet containing high fat. The mice with high-fat-diet-induced obesity were separated into groups by body weight before beginning the experiment. Compounds 3, 21-25 according to the present invention were prepared in distilled water containing 0.01% Tween80 to a dosage of 100 nmol/kg and as indicated in Table 11 subcutaneously injected once every 3 days for a total of 2 weeks. Body weight and food intake was measured once per day at the same time each day. Body weight loss efficacy of Compound 3 and Compounds 21-25 was compared. The results are shown in FIGS. 7a through 7d.

TABLE 11

| Group | Drug and dose administered | Method of administration | |
|---|---|---|---|
| Experimental | Compound 3, 100 nmol/kg/Q3D<br>Compound 21, 100 nmol/kg/Q3D<br>Compound 22, 100 nmol/kg/Q3D<br>Compound 23, 100 nmol/kg/Q3D<br>Compound 24, 100 nmol/kg/Q3D<br>Compound 25, 100 nmol/kg/Q3D | S.C | once every 3<br>days × 5 |

At same dosage, Compounds 23 and 25 had higher cumulative food intake compared to Compound 3. Compounds 21 and 22 showed similar cumulative food intake as Compound 3. Compound 3 showed similar or better body weight loss compared to Compounds 21, 23 and 25. Compound 25 was confirmed to have better body weight loss efficacy than Compound 3. On the other hand, Compound 24, which showed somewhat weak action on glucagon receptor compared to other compounds in in vitro assay, showed significant body weight loss efficacy, at about 13.4% against initial body weight, showing inferior body weight loss efficacy compared to Compound 3. Compound 25 showed similar level of body weight loss efficacy to Compound 3 but had lower cumulative food intake. On the other hand, Compound 22 showed similar body weight loss efficacy to Compound 3 and similar cumulative food intake. Acylated oxyntomodulin cyclic peptide analogs showed different body weight loss efficacy patterns depending on their structures.

<Experimental Example 9> Body Weight Loss Efficacy Evaluation by 2-Week Repeated Injection of Peptide of Present Invention Continuing from Experimental Example 8, this experiment was conducted to compare acylated oxyntomodulin peptide analogs of the present invention in low doses. Male laboratory mice (C57BL/6 mouse) were given diet containing high fat. The mice with high-fat-diet-induced obesity were separated into groups by body weight before beginning the experiment. Compounds 3 and 22 according to the present invention were prepared in distilled water containing 0.01% Tween80 to a dosage of 10 nmol/kg or 30 nmol/kg and as indicated in Table 12 injected subcutaneously once every 3 days for a total of 2 weeks. Body weight and food intake was measured once per day, at the same time each day. Body weight loss efficacy of Compound 3 and Compound 22 was compared. The results are shown in FIGS. 8a and 8b.

TABLE 12

| Group | Drug and dose administered | Method of administration | |
|---|---|---|---|
| Experimental | Compound 3, 10 nmol/kg/Q3D<br>Compound 3, 30 nmol/kg/Q3D<br>Compound 22, 10 nmol/kg/Q3D<br>Compound 22, 30 nmol/kg/Q3D | S.C | once every 3<br>days × 5 |

At the same dosage, Compound 22 showed higher cumulative food intake compared to Compound 3. Compound 22 at 10 nmol/kg showed similar level of cumulative food intake as vehicle control group but body weight loss efficacy of 7.5%. Furthermore, Compound 22 at 30 nmol/kg had higher food intake than Compound 3 at the same dose but had similar levels of body weight loss efficacy. It can be inferred that Compound 22 is affected more by the efficacy resulting from glucagon receptor activation compared to Compound 3.

<Experimental Example 10> Body Weight Loss Efficacy Evaluation by 5-Day Repeated Injection of Peptide of Present Invention This experiment was conducted to compare the body weight loss efficacy of acylated oxyntomodulin peptide analog of the present invention with commercially available diabetes/obesity treatment and an oxyntomodulin peptide analog lead compound currently in development. Male laboratory mice (C57BL/6 mouse) were given diet containing high fat. The mice with high-fat-diet-induced obesity were grouped by body weight before beginning the experiment. Compound 3 of the present invention was prepared in distilled water containing 0.01% Tween80 to dose of 30 nmol/kg. As comparative examples, Liraglutide (commercially available diabetes/obesity treatment) and MEDI0382 (in clinical trial) were prepared in the same vehicle to a dose of 30 nmol/kg. Then, they were subcutaneously injected once per day for 4 days total, as indicated in Table 13. Body weight and food intake was measured once per day, at the same time each day. Body weight loss efficacy of the analog was compared with Liraglutide and MEDI0382. The results are shown in FIGS. 9a and 9b.

TABLE 13

| Group | Drug and dose administered | Method of administration | |
|---|---|---|---|
| Comparison | Liraglutide, 30 nmol/kg/QD | S.C | once a day × 4 |
| | MEDI0382, 30 nmol/kg/QD | | |
| Experimental | Compound 3, 30 nmol/kg/QD | | |

Among the three substances at same dose, the Compound 3 group showed most body weight loss from baseline (Compound 3: 18.6%, Liraglutide: 12.7%, MEDI0382: 8.0%).

<Experimental Example 11> Body Weight Loss Efficacy Evaluation by 4-Week Repeated Injection of Peptide According to Present Invention This experiment was conducted to compare the body weight loss efficacy of acylated oxyntomodulin peptide analogs according to the present invention with commercially available diabetes treatment. Male obese and diabetic laboratory mice (FATZO mouse) were given diet containing high fat, and were grouped by body weight, body fat, non-fasting blood glucose, and glycated hemoglobin (HbA1c) before experiment. Compounds 3 and 22 according to the present invention were prepared in distilled water containing 0.01% Tween80 to a dose of 30 nmol/kg or 100 nmol/kg. Semaglutide, commercially available diabetes treatment, was prepared in the same vehicle to a dose of 100 nmol/kg. Then, they were given subcutaneously once every 3 days for a total of 4 weeks, as indicated in Table 14. Body weight and food intake was measured once per day, at the same time each day. Body fat was measured at 4 weeks before autopsy to compare the body weight and body fat reduction efficacy of oxyntomodulin peptide analogs of the present invention against Semaglutide. The results are shown in FIGS. 10a through 10c.

TABLE 14

| Group | Drug and dose administered | Method of administration | |
|---|---|---|---|
| Comparison | Semaglutide, 100 nmol/kg/Q3D | S.C | once every 3 days × 10 |
| Experimental | Compound 3, 30 nmol/kg/Q3D | | |
| | Compound 3, 100 nmol/kg/Q3D | | |
| | Compound 22, 30 nmol/kg/Q3D | | |
| | Compound 22, 100 nmol/kg/Q3D | | |

At both same and lower dosage (100 and 30 nmol/kg respectively), Compounds 3 and 22 of the present invention shows highly superior body weight reduction efficacy against Semaglutide despite higher cumulative food intake. This is inferred to be a result of the mechanism of action of oxyntomodulin peptide analog according to the present invention being a dual agonist of GLP-1 and glucagon receptors, whereas Semaglutide is a GLP-1 receptor agonist.

<Experimental Example 12> Oral Glucose Tolerance Test in Mice of Peptide According to Present Invention In this experiment, glucose tolerance improvement effect in male laboratory mice (C57BL/6 mouse) of acylated oxyntomodulin peptide analogs according to the present invention was evaluated as improvement of postprandial glycemic control. Laboratory mice were fasted the day before the experiment. Then, Compound 3 or 22 or 25 according to the present invention was prepared in distilled water containing 0.01% Tween80 and injected subcutaneously 30 minutes before glucose loading. Glucose solution was orally administered 30 minutes after the injection of oxyntomodulin peptide analog. Whole blood glucose was measured via tail vein immediately before administering the drug and glucose, and for 2 hours after glucose loading at designated times. From the results, the area under the curve (AUC) of the blood glucose curve over time was produced to calculate the ratio of blood glucose AUC of the analog and comparison against glucose control as percentages to evaluate the efficacy of glucose tolerance improvement. Experiments were conducted separately for each compound. Compound 3 at 30 nmol/kg was used as comparison for Compound 22 or 25. The combined results are shown in FIG. 11.

The peptide analogs showed significant, dose-dependent reduction of blood glucose AUC at and above 30 nmol/kg. In particular, Compound 25 showed significant glucose tolerance improvement efficacy and three times superior glucose tolerance improvement efficacy compared to Compounds 3 and 22 in all dose groups evaluated.

<Experimental Example 13> Glycemic Control Efficacy Evaluation by 6-Week Repeated Injection of Peptide According to Present Invention The present invention was conducted to compare the glycemic control efficacy of acylated oxyntomodulin peptide analogs according to the present invention with commercially available diabetes treatment. Male laboratory diabetes mouse models (db/db mouse) were grouped by non-fasting glucose level, glycated hemoglobin (HbA1c), and body weight before experiment. Compound 3 according to the present invention was prepared in distilled water containing 0.01% Tween80 to a dose of 100 nmol/kg. Commercially available Semaglutide was prepared in same vehicle to a dose of 100 nmol/kg. Afterwards, they were injected subcutaneously once every 3 days for a total of 6 weeks as indicated in Table 15. Non-fasting glucose, body weight, and food intake were measured once a week, 24 hours after drug administration. Glycated hemoglobin was measured at 3, 5 and 6 weeks. The glycemic control efficacy of oxyntomodulin peptide analog according to the present invention was compared with that of Semaglutide. The results are shown in FIGS. 12a and 12b.

TABLE 15

| Group | Drug and dose administered | Method of administration | |
|---|---|---|---|
| Comparison | Semaglutide, 100 nmol/kg/Q3D | S.C | once every 3 days × 16 |
| Experimental | Compound 3, 100 nmol/kg/Q3D | | |

Initially, Compound 3 of the present invention showed similar or lower efficacy compared to Semaglutide at same dose (100 nmol/kg). However, after long-term administration, Compound 3 showed better glycemic control efficacy than Semaglutide. The vehicle control group had a final non-fasting blood glucose of 581 mg/dL, showing very severely diabetic condition. On the other hand, Semaglutide showed a final non-fasting glucose of 342 mg/dL; Compound 3 had a final non-fasting blood glucose of 274 mg/dL, showing significant inhibition of glucose elevation. Final glycated hemoglobin (HbAlc) of the vehicle control group was 5.15% points higher than initial level. In comparison, Semaglutide HbAlc increased by 2.65% points, and Compound 3 HbAlc only 1.73% points, confirming efficacy in glycated hemoglobin elevation inhibition. Therefore, the acylated oxyntomodulin peptide analog according to the present invention showed superior efficacy to Semaglutide in delaying the onset of diabetes.

<Experimental Example 14> Glycemic Control Efficacy Evaluation by 4-Week Repeated Injection of Peptide According to Present Invention This is the same experiment as Experimental Example 11. It was conducted to compare glycemic control efficacy of acylated oxyntomodulin peptide analog according to the present invention in comparison to commercially available diabetes treatment. Male obese and diabetic laboratory mice (FATZO mouse) were given diet containing high fat and were grouped by body weight, body fat, non-fasting glucose, and glycated hemoglobin (HbAlc) before experiment. Compounds 3 and 22 according to the present invention were prepared in distilled water containing 0.01% Tween80 to a dosage of 30 nmol/kg or 100 nmol/kg. Commercially available Semaglutide was prepared in same vehicle to a dose of 100 nmol/kg. As indicated in Table 16, both were injected subcutaneously once every 3 days for a total of 4 weeks. Body weight and food intake was measured once per day at the same time each day. Non-fasting glucose was measured approximately every 10 days, 24 after administration. Glycated hemoglobin was measured before autopsy at 4 weeks. Glycemic control efficacy of oxyntomodulin peptide analog of the present invention was compared with Semaglutide. The results are shown in FIGS. 13a and 13b.

TABLE 16

| Group | Drug and dose administered | Method of administration | |
|---|---|---|---|
| Comparison | Semagiutide, 100 nmol/kg/Q3D | S.C | once every 3 days × 10 |
| Experimental | Compound 3, 30 nmol/kq/Q3D | | |
| | Compound 3, 100 nmol/kg/Q3D | | |
| | Compound 22, 30 nmol/kg/Q3D | | |
| | Compound 22, 100 nmol/kg/Q3D | | |

The groups administered with Compounds 3 and 22 of the present invention showed outstanding glycemic control efficacy and glycated hemoglobin elevation inhibition at similar levels as Semaglutide. In addition to the body weight loss effect shown in Experimental Example 11, the oxyntomodulin peptide analog of the present invention is shown to also have glycemic control effect.

The invention claimed is:

1. An oxyntomodulin peptide analog of the following formula I:

(SEQ ID NO.49)
His-$X_1$-Gln-Gly-Thr-Phe-Thr-Ser-$X_2$-$X_3$-$X_4$-$X_5$-$X_6$-$X_7$-$X_8$-$X_9$-Arg-Arg-Ala-$X_{10}$-Asp-Phe-Val-Gln-Trp-Leu-$X_{11}$-$X_{12}$-$X_{13}$-$X_{14}$-$X_{15}$-$X_{16}$, wherein:

$X_1$ is Aib (aminoisobutyric acid);

$X_2$ is Asp;

$X_3$ is Tyr or Z;

$X_4$ is Ser;

$X_5$ is Lys;

$X_6$ is Tyr;

$X_7$ is Leu;

$X_8$ is Asp;

$X_9$ is Ser, Aib (aminoisobutyric acid) or Z;

$X_{10}$ is Gln or Z;

$X_{11}$ is Met or Leu;

$X_{12}$ is Asn or Arg;

$X_{13}$ is Thr or Ala;

$X_{14}$ is Lys;

$X_{15}$ is absent;

$X_{16}$ is absent;

C-terminal amino acid may optionally be amidated; wherein one of $X_3$, $X_9$, and $X_{10}$ is Z;

Z is modified Lys to which $Z_1$-$Z_2$ of the following formulas is attached;

$Z_1$ is Formula (1); and

Structural Formula (1) is

[chemical structure]

$n_1 = 1$-$4$
$n_2 = 1$-$2$

Structural Formula (2) is

[chemical structure]

$R_1, R_2 =$ H or ——$CH_2OH$ $m = 1$-$3$

Structural Formula (3) is

[chemical structure] ; and $p = 12, 14, 16$ or $18$

Structural Formula (4) is

[chemical structure]

$R_3 =$ OH or $NH_2$
$p = 12, 14, 16$ or $18$ $Z_2$ is Formula (3);

[chemical structure] (3)

$p = 12, 14, 16,$ or $18$ wherein * of Formula (1) is directly bound to a side chain of Lys, and wherein  of Formula (1) and  of formula (3) are bond between $Z_1$ and $Z_2$.

2. The oxyntomodulin peptide analog of claim 1, wherein $X_{11}$ is Leu, $X_{12}$ is Arg, and $X_{13}$ is Ala.

3. An oxyntomodulin peptide analog of claim 1, wherein
$X_{10}$ is Gln;
$X_{11}$ is Met;
$X_{12}$ is Asn; and
$X_{13}$ is Thr.

4. An oxyntomodulin peptide analog of claim 1, wherein $n_2$ of Formula (1) is 1.

5. The oxyntomodulin peptide analog of claim 1, wherein said peptide analog is Compound 2 (SEQ ID NO: 3), Compound 3 (SEQ ID NO: 4), Compound 6(SEQ ID NO: 7), Compound 9 (SEQ ID NO: 10), Compound 10 (SEQ ID NO: 11), Compound 12 (SEQ ID NO: 13), Compound 15 (SEQ ID NO: 16), Compound 16 (SEQ ID NO: 17), Compound 17 (SEQ ID NO: 18), or Compound 18 (SEQ ID NO: 19).

6. A pharmaceutical composition comprising the peptide analog of claim 1 and a pharmaceutically acceptable excipient.

7. The pharmaceutical composition of claim 6, wherein, in the oxyntomodulin peptide analog of formula I,
$X_{10}$ is Gln;
$X_{11}$ is Met;
$X_{12}$ is Asn; and
$X_{13}$ is Thr.

8. A method of treating a subject with obesity or overweight comprising administering an effective amount of the pharmaceutical composition of claim 6 to the subject.

9. The method of claim 8, wherein the subject suffers from non-insulin-dependent diabetes.

* * * * *